United States Patent
Carrigan et al.

(10) Patent No.: US 9,869,617 B2
(45) Date of Patent: Jan. 16, 2018

(54) AUTOMATED METHODS, KITS, AND SYSTEMS FOR CLARIFYING OBFUSCATING PIGMENTS IN HISTOLOGY SAMPLES

(71) Applicant: Ventana Medical Systems, Inc., Tucson, AZ (US)

(72) Inventors: Patricia Carrigan, Scottsdale, AZ (US); James Grille, Tucson, AZ (US); Greg Martin, Oro Valley, AZ (US); Mark Robida, Tucson, AZ (US); Patrick C. Roche, Tucson, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 0 days.

(21) Appl. No.: 14/432,962

(22) PCT Filed: Oct. 7, 2013

(86) PCT No.: PCT/EP2013/070758
§ 371 (c)(1),
(2) Date: Apr. 1, 2015

(87) PCT Pub. No.: WO2014/056812
PCT Pub. Date: Apr. 17, 2014

(65) Prior Publication Data
US 2015/0276563 A1    Oct. 1, 2015

Related U.S. Application Data

(60) Provisional application No. 61/711,112, filed on Oct. 8, 2012.

(51) Int. Cl.
G01N 1/30 (2006.01)
G01N 1/31 (2006.01)

(52) U.S. Cl.
CPC .............. *G01N 1/30* (2013.01); *G01N 1/312* (2013.01); *G01N 2001/302* (2013.01)

(58) Field of Classification Search
None
See application file for complete search history.

(56) References Cited

U.S. PATENT DOCUMENTS

| | | | |
|---|---|---|---|
| 5,232,664 A | 8/1993 | Krawzak et al. | |
| 6,296,809 B1 | 10/2001 | Richards et al. | |
| 6,465,208 B1 * | 10/2002 | Rogers ................... | G01N 1/30 435/4 |
| 6,537,818 B2 | 3/2003 | Richards et al. | |
| 6,855,552 B2 | 2/2005 | Towne et al. | |
| 7,404,927 B2 | 7/2008 | Lemme et al. | |
| 7,935,534 B2 | 5/2011 | Lemme et al. | |
| 9,091,691 B2 * | 7/2015 | Lohse ................... | G01N 33/581 |
| 2003/0100043 A1 | 5/2003 | Kalra et al. | |
| 2004/0067548 A1 | 4/2004 | Kawashima et al. | |
| 2004/0121485 A1 | 6/2004 | Hopkins et al. | |
| 2006/0252025 A1 | 11/2006 | Nitta et al. | |
| 2008/0227143 A1 | 9/2008 | Kosmeder et al. | |
| 2008/0261266 A1 | 10/2008 | Kram et al. | |
| 2009/0017050 A1 | 1/2009 | Powell et al. | |
| 2011/0305842 A1 | 12/2011 | Kram | |

FOREIGN PATENT DOCUMENTS

| | | |
|---|---|---|
| CA | 2179368 A1 | 12/1997 |
| WO | 2010078176 A1 | 7/2010 |
| WO | 2011060387 A1 | 5/2011 |
| WO | 2011133625 A1 | 10/2011 |
| WO | 2012024185 A1 | 2/2012 |

OTHER PUBLICATIONS

Momose, M. et al., "Re-evaluation of melanin bleaching using warm diluted hydrogen peroxide for histopathological analysis," Pathology International, 2011: 61, pp. 345-350.

* cited by examiner

*Primary Examiner* — Ralph Gitomer
(74) *Attorney, Agent, or Firm* — Nguyen & Tarbet Patent Law Firm

(57) ABSTRACT

Methods, kits, and systems for clarifying obfuscating pigments in histology samples such as an automated method of treating a histology sample with a clarifying reagent so that the clarifying reagent, contacts the sample and the pigments within the sample are decolorized, thus alleviating staining obfuscations associated with pigments. Decolorizing the pigments within the sample enables the histology sample to be interpretable by a qualified reader. An antigen retrieval step is performed after the clarification step.

24 Claims, 17 Drawing Sheets
(16 of 17 Drawing Sheet(s) Filed in Color)

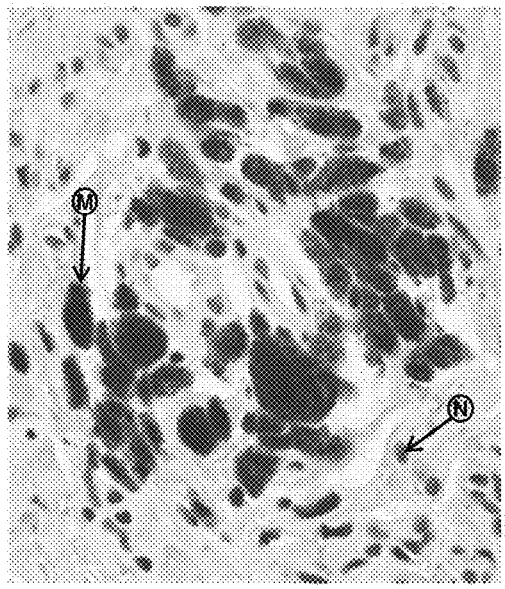 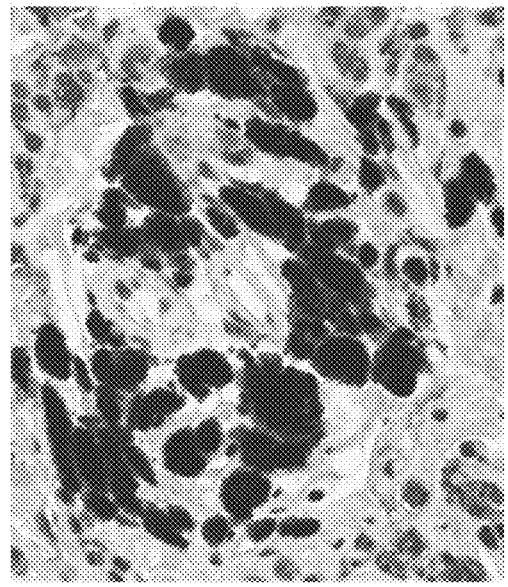
FIG. 1(A)  FIG. 1(B)
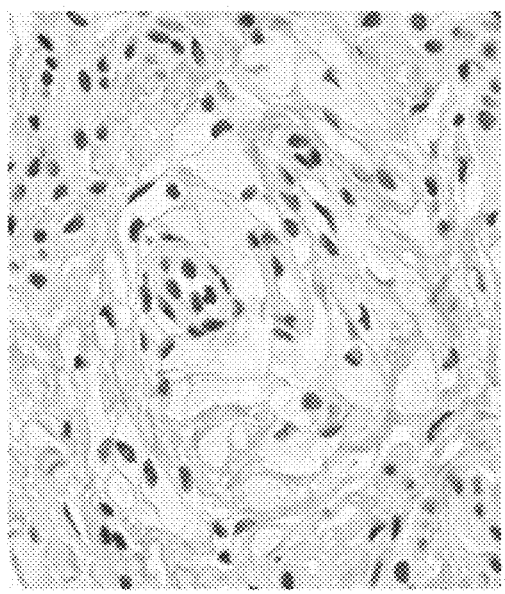 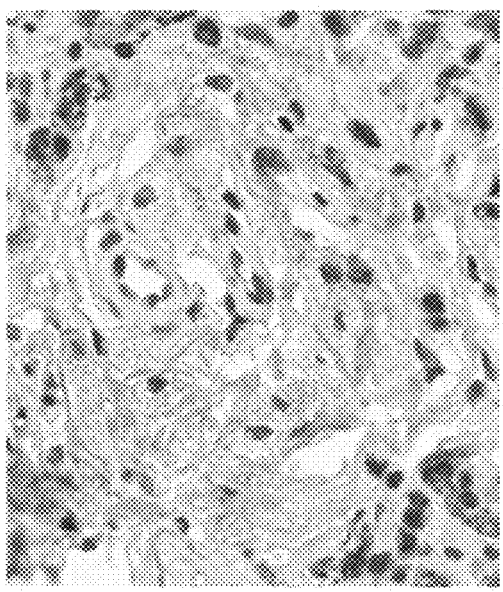
FIG. 1(C)  FIG. 1(D)

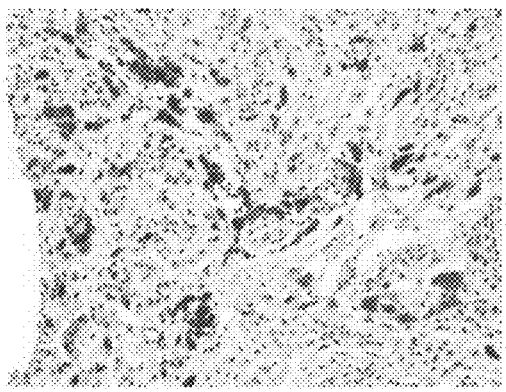
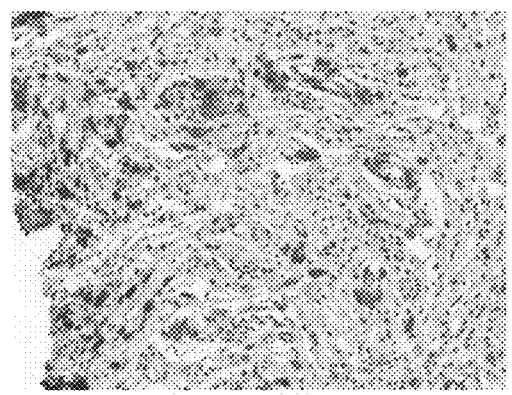
FIG. 6(A)　　　　　　　　FIG. 6(B)
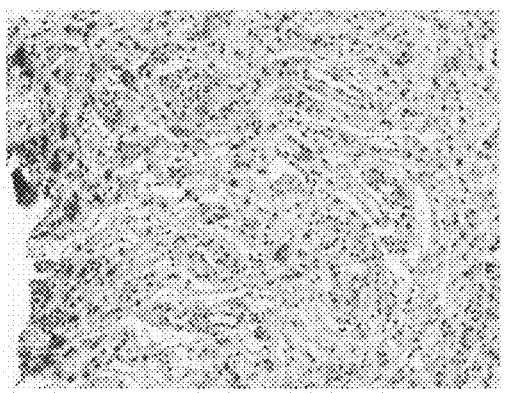
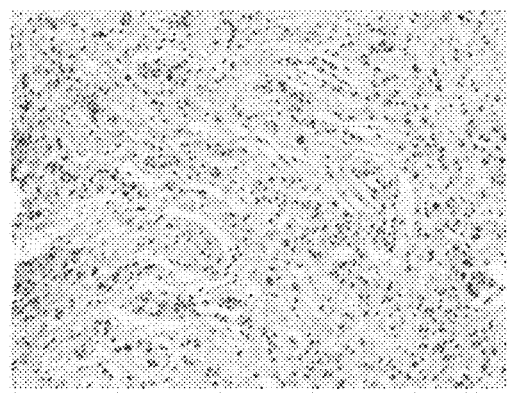
FIG. 6(C)　　　　　　　　FIG. 6(D)
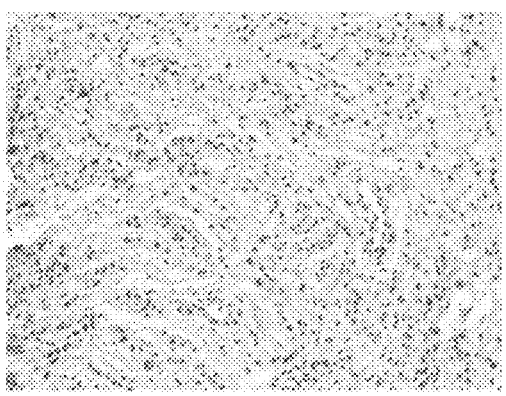
FIG. 6(E)

AUTOMATED METHODS, KITS, AND SYSTEMS FOR CLARIFYING OBFUSCATING PIGMENTS IN HISTOLOGY SAMPLES

FIELD

This disclosure relates to methods, kits, and systems for clarifying biological samples where the samples include pigments.

BACKGROUND

Biological samples, for example histology samples, may be examined in histopathological examination by light microscopy using bright-field illumination. Molecular pathology is the examination, at a molecular level, of biomolecules associated with disease. From a histopathological examination, important information about patient diagnosis, prognosis, and treatment options can be elucidated. Pathologists study the histopathologic architecture, tissue morphology, and/or signals associated with the detection of particular biomolecules (e.g. nucleic acid or proteins). A number of assays presently available detect and/or quantify proteins (i.e. immunohistochemistry (IHC)), nucleic acids (i.e. in situ hybridization (ISH)), carbohydrates (i.e. histochemistry (HC)), and enzymes (i.e. enzyme histochemistry (EHC)).

Histopathological examination of pigment-containing samples is difficult because pigments can obscure the evaluation of the samples. For example, excessive amounts of melanin pigments hamper histopathological assessments of melanocytic lesions by obscuring cellular morphology, obscuring chromogenic staining, and hindering antibody-antigen interactions.

SUMMARY

Methods, kits, and systems for treating samples containing obfuscating pigments are disclosed. The method includes applying a clarifying reagent to the sample so that the obfuscating pigments within the sample are decolorized. Decolorizing the obfuscating pigments enhances pathologists' ability to examine the sample.

In illustrative embodiments, an automated method of treating a sample mounted on a substrate to alleviate staining obfuscations associated with pigments within the sample is disclosed. The method includes placing the substrate upon which the sample is mounted on an automated instrument and applying a clarifying reagent so that the clarifying reagent contacts the sample and pigments within the sample are decolorized. The method further comprises applying a rinsing reagent so that the clarifying reagent is substantially removed from the sample and applying a chromogenic reagent so that the sample is specifically stained. Pigments within the sample are decolorized by the clarifying reagent so that the specifically stained sample is interpretable by a qualified reader.

In other illustrative embodiments, disclosed is a kit for decolorizing obfuscating pigments in a sample. The kit includes a reagent bottle and a clarifying reagent deposited in the reagent bottle. The clarifying reagent comprises an aqueous solution of hydrogen peroxide and the reagent bottle is configured to be operably connected to an automated slide staining apparatus such that the automated slide staining apparatus controls the application of the clarifying reagent so that the clarifying reagent contacts the sample.

In further illustrative embodiments, disclosed is a system for alleviating specific signal obfuscation for a histopathological sample containing pigments. The system includes an automated instrument, a clarifying reagent, and a chromogenic reagent. The automated instrument is configured to receive the histopathological sample adhered to a substrate, to deliver the clarifying reagent and the chromogenic reagent to the sample, and to provide heating and mixing to the clarifying reagent and the chromogenic reagent delivered to the sample. The clarifying reagent is configured to contact the histopathological sample and render the obfuscating pigments decolorized. The chromogenic reagent is configured to contact the histopathological sample and deposit a specific signal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1(A)-1(D) are photomicrographs of serial microtome sections of a sample (melanoma tissue sample), wherein (A) shows obfuscations associated with pigments within the sample, dark bodies evident within the photomicrograph are naturally occurring pigments (e.g. melanin), (B) shows the sample containing obfuscating pigments specifically stained with 3,3'-diamino-benzidine (DAB), the staining is specific to a cancer marker, the dark bodies associated with melanin and the DAB staining being difficult to distinguish, (C) shows the sample treated with a clarifying reagent, the absence of dark bodies associated with melanin is evident, and (D) shows the sample treated with the clarifying reagent and specifically stained with DAB, wherein the specific staining is evident.

FIG. 6(A)-(E) are photomicrographs of serial microtome sections of a different melanoma tissue sample showing the effect of incubation time on clarification results under fixed temperature and peroxide conditions.

DETAILED DESCRIPTION

Figure 2A:
FIG. 2(A)-2(D) are photomicrographs of serial microtome sections of a different melanoma tissue sample, wherein (A) shows obfuscations associated with pigments within the sample, the sample being a darkly pigmented with melanin, (B) shows the sample containing obfuscating pigments specifically stained with DAB, the staining is specific to a cancer marker, the dark bodies associated with the melanin and the DAB staining being visible and difficult to distinguish, (C) shows the sample subsequent to treatment with a clarifying reagent, the absence of dark bodies associated with melanin is evident, and (D) shows the sample treated with the clarifying reagent and specifically stained with DAB, the dark bodies associated with melanin are absent and thus do not obscure the specific DAB staining.

Histopathological examination of pigment-containing biological samples can be challenging due to the pigments obscuring visualization of chromogenic signals and cell morphology. In particular, biological samples which include pigments, such as intracellular melanin granules, can be difficult to assess due to the presence of granules. These granules can obscure cell morphology and cause direct physical masking of antibody-antigen interaction. One aspect of the present disclosure is that automated clarifying procedures for these kinds of biological samples have been discovered which enable improved visualization of cellular morphology and reveal masked portions of the sample for antibody-antigen interaction. These automated clarifying procedures enhance sample visualization while mitigating cell morphology and antigenic/target degradation.

Pigments within cells can obscure the visualization of the absorbance of histological chromogens. As such, IHC, ISH, and cellular staining (e.g. hematoxylin and eosin) signals are obfuscated and pathological evaluations may be compromised. Pigments are characterized by absorbing visible light and by a lack of solubility in the local medium. Pigments associated with biological samples may be classified as exogenous, coming from outside of the body, or endogenous, created by the body. One exemplary exogenous pigment is carbon (e.g. coal dust). Carbon deposits are common air pollutants in urban environments and anthracosis is the accumulation of this carbon in the tissues of the lungs. Exogenous pigments common in epidermal tissues include those used for tattoos. Endogenous pigments include lipochrome, melanin, homogentisic acid, hemosiderin, and bilirubin. Lipochrome is composed of polymers of lipids and phospholipids. Melanin, which is formed when tyrosinase catalyzes oxidation of tyrosine to dihydroxyphenylalanine in melanocytes, is common in epidermal tissues. Homogentisic acid, known to cause pigmentation known as ochronosis, occurs in patients with alkaptonuria. Hemosiderin represents aggregates of ferritin micelles and can be caused by any form of hemorrhage including the common bruise. Bilirubin is the major pigment found in bile.

Melanin is a biological pigment comprising a highly heterogeneous polymer that includes various monomer units selected from dihydroxyindole, dihydroxyindole carboxylic acids, benzothiazine, and/or their reduced forms. The monomer units are linked and/or crosslinked through a variety of bonds to form opaque, insoluble, and complex polymers with diverse properties. While the level of pigmentation in biological samples varies continuously across a spectrum of concentrations, a particular tissue is often characterized as either lightly, moderately, or heavily pigmented. While any level of pigmentation can obscure histopathological assessment, pigment obfuscation increases with pigment concentration. Melanin can obscure cellular morphology and specific staining and hinder antibody-antigen interactions. By masking antibody-antigen or ISH interactions and obscuring signals generated therefrom, melanin can affect gross positive/negative analysis and can lead to an errant analysis of intensity and percent positive cells.

In illustrative embodiments, an automated method of treating a sample mounted on a substrate to alleviate staining obfuscations associated with pigments within the sample includes placing the substrate upon which the sample is mounted on an automated instrument, applying a clarifying reagent so that the clarifying reagent contacts the sample and the pigments within the sample are decolorized, applying a rinsing reagent so that the clarifying reagent is substantially removed from contacting the sample, and applying a chromogenic reagent so that the sample is specifically stained. The pigments within the sample are decolorized so that the specifically stained sample is interpretable by a qualified reader.

In further illustrative embodiments, the method of treating a sample includes applying a clarifying reagent so that the clarifying reagent contacts the sample and the pigments within the sample are decolorized. In one embodiment, applying the clarifying reagent includes the clarifying reagent contacting the sample for a time between about 2 minutes and about 2 hours, between about 4 minutes and about 1.5 hours, between about 6 minutes and about 1 hour, or between about 8 minutes and about 0.5 hours. A challenge in the modern histopathology laboratory is the turn-around-time from receiving a sample to delivering the sample in a condition appropriate for reading. Pigment containing samples were known to have longer turn-around-times as they required a manual bleaching procedure prior to staining. In addition to extended duration of many of the manual bleaching processes (often greater than 24 hours), the samples were often batched so that a number of the samples could be treated concurrently. Turn-around-time is enhanced according to methods, kits, and systems of the present disclosure as the clarifying step is incorporated into a fully automated method. Furthermore, the manner in which the automated instrument applies the clarifying reagent, applies heat to the sample, and can repeat as necessary provides drastically reduced times for the clarifying step. In particular, processes formerly taking 24-48 hours can be completed, as described herein, in less than 2 hours. Furthermore, the systematic evaluation of clarifying rate across a large number of samples has led to the discovery that even severely pigmented samples can be efficiently decolorized in less than 2 hours.

In illustrative embodiments, the clarifying reagent includes about 1% to about 12% hydrogen peroxide (v/v), about 2% to about 10% hydrogen peroxide (v/v), or about 3% to about 9% hydrogen peroxide (v/v). In another embodiment, the clarifying reagent includes a phosphate buffer at a concentration of about 0.001 M to about 0.5 M, about 0.01 M to about 0.1 M, or about 0.05 M. In another embodiment, the clarifying reagent is buffered at a pH of between about 3 to about 11, between about 4 to about 10, between about 5 to about 9, between about 6 to about 8, or about 7. In another embodiment, the clarifying reagent includes a Sorensen's phosphate buffer at a concentration of about 0.001 M to about 0.5 M, about 0.01 M to about 0.1 M, or about 0.05 M and a pH of between about 4 to about 10, between about 5 to about 9, between about 6 to about 8, or about 7. In another embodiment, the clarifying reagent is morphologically neutral over the predetermined time so that a qualified reader would conclude that the samples exhibits morphological characteristics consistent with those of the sample prior to the applying the clarifying reagent.

In illustrative embodiments, the method includes applying a rinsing reagent so that the clarifying reagent is substantially removed from contacting the sample. One aspect of the present disclosure is that methods, kits, and systems enable the clarification of pigment-containing samples on automated instruments. Automated instruments, as disclosed herein, are capable of delivering rinsing reagents between various procedural steps to enhance the performance of the subsequent steps. The rinsing step here removes unreacted clarifying reagent and prepares the sample for specific staining.

In illustrative embodiments, a method of the present disclosure includes applying heat to the substrate so that the sample and the clarifying reagent are at a predetermined temperature while in contact. In one embodiment, the temperature and time are precisely controlled through the automated instrument. Precision time and temperature steps enable the methods described herein to deliver superior reproducibility and control to the method steps. The reproducibility in the method steps enables the results of the process to be reproducible from run to run and laboratory to laboratory. Furthermore, the delivery of the reagents by the automated instrument reduces human error and the cost of human labor. While reducing human error and the cost of human labor, automation of the process steps is safer for the laboratory workers as the handling of hot and oxidative compositions is now removed from the technician and performed by the automated instrument. In one embodiment, the predetermined temperature is between about 35° C. and about 100° C., between about 40° C. and about 90° C., between about 45° C. and about 80° C., or between about 50° C. and about 70° C.

One aspect of the present disclosure is that the temperature control provided by the automated instrument provides superior results that were heretofore not possible. For example, the rate of heating provided by the automated instrument contributes to the aforementioned turn-around-time performance. In one embodiment, the temperature of the sample can be increased from 37° C. to 100° C. within eight (8) minutes and cooled from 100° C. to 50° C. within eight (8) minutes, as measured at the center of the heating platform. In another embodiment, the temperature of the sample can be increased from 37° C. to 100° C. within four (4) minutes and cooled from 100° C. to 37° C. within eight (8) minutes. Another aspect of the present disclosure is that the temperature across the sample can be uniformly controlled and such uniform control enhances the consistency of the decolorization of the sample so that the pigments are uniformly clarified across a sample. In one embodiment, the uniformity in temperature across the slide is less than about plus or minus 2° C. at 37° C. and less than about plus or minus about 4° C. at 100° C. In another embodiment, the uniformity in temperature across the slide is less than about plus or minus 2° C. at 37° C. and less than about plus or minus about 3° C. at 100° C.

As described herein, embodiments of automated methods described herein include a sample mounted on a substrate. In one embodiment, the substrate is a glass slide. In another embodiment, the glass slide is a glass microscope slide. In illustrative embodiments, a heated slide platform is used for applying heat to the glass slide. One aspect of the present disclosure is that the heated slide platform heats the slide such that the resulting clarification exhibits superior results. Other methods of heating have been described which include heating baths of oxidative chemicals using microwave radiation, ovens, or temperature baths. Slide platforms provide superior heating to the sample by at least (1) delivering heat directly to the substrate, which then directly heats the sample and the clarifying reagent in contact therewith, (2) delivering heat uniformly across the substrate so that each portion of the sample reaches a substantially equivalent predetermined temperature, (3) applying the heat directly to the substrate, as opposed to the sample, so that the sample does not experience direct heating and the concomitant over-heating which can damage the sample, and (4) delivering heat to the substrate and correspondingly to the sample, at a rate higher than can be delivered through a bath. In one embodiment, the sample is placed on a top surface of a slide and the slide is then placed on top of the heated slide platform, so that the bottom surface of the slide is in contact with the heated slide platform. The heated slide platform, via conduction, heats the bottom portion of the slide.

Manual or automated processes that include the use of reagent baths for treating histopathology samples are known to present patient safety risks. Substantial evidence has been amassed demonstrating that methods that include reusing reagent baths for histopathology samples may result in cross-contamination of samples which can lead to misdiagnosis. A percentage of samples exposed to clarifying compositions in a bath will lose adhesion to the substrate and remain in the bath after the substrate is removed. This problem is exacerbated by the nature of clarifying solutions; it was discovered that clarifying solutions cause a greater percentage of samples to loose adhesion than traditional staining reagents. Reuse of the bath after the first substrate is withdrawn is inferior to the present technology for several reasons. It is possible that the first sample, having lost adhesion to the first substrate may adhere to the second substrate so that substrate includes samples from multiple sources. This can lead to misdiagnosis of the patient or the need to duplicate the process with a fresh sample. Reusing the reagent bath also subjects the second sample to conditions different than the first sample because reagent is consumed by exposure to the first sample. That is, the nature of the bath composition changes over time in response to its repeated use. This degradation in reagent quality is compounded by the nature of efficient clarifying solutions. Specifically, clarifying reagents tend to be highly oxidative compositions which are maintained at elevated temperatures. Accordingly, the present disclosure describes methods, kits, and systems that are able to deliver superior reproducibility, performance, and patient safety by being bath-free. In one embodiment, applying the clarifying reagent does not include submersing the substrate in a bath. In illustrative embodiments, the system and kit of the present disclosure include a clarifying composition in a dispenser configured for automatic dispensing. In one embodiment, the automated method is devoid of steps requiring a user to handle the substrate between placing the substrate upon which the sample is mounted on the automated instrument and contacting the sample with the chromogenic reagent such that the sample is specifically stained.

In one embodiment, the method includes maintaining the temperature of the reagent at a storage temperature prior to applying the clarifying reagent to the sample. In one embodiment, the storage temperature is between about 4° C. and about 37° C. so that the stability of the clarifying solution is maintained for extended periods of time. In other embodiments, the storage temperature is room temperature. In further embodiments, the clarifying reagent has a shelf-life, under appropriate storage conditions, of greater than about 12 months, greater than about 18 months, or greater than about 24 months. The extended shelf-life is an advantage over baths in that the baths cannot be maintained for extended periods without significant degradation. Another aspect of the system, kit, and methods of the present disclosure is that a bath-free configuration enables the clarifying reagent to be sealed from the atmosphere. Solutions in baths are subject to differential vaporization of the various components therein so that the concentrations shift over time. Furthermore, solutions in baths interact with air-borne molecules which can change the pH, purity, or clarifying capacity of the solutions. For example, carbon dioxide in ambient air can be dissolved in a bath and shift the pH through the formation of carbonic acid. Similarly, air-borne dust can contact an open bath solution to reduce its purity. Those air-borne constituents may also react with clarifying reagent so as to reduce the availability of the reagent for clarifying tissue. This is especially true for highly oxidizing reagents which may indiscriminately oxidize with contaminants. The use of dispensers for the clarifying reagent provides superior results within the scope of the present disclosure.

In illustrative embodiments, applying the clarifying reagent includes an amount of the clarifying reagent of between about 0.05 mL and about 3 mL, between about 0.1 mL and about 1.5 mL, between about 0.2 mL and about 1 mL, or between about 0.3 mL and about 0.5 mL. In contrast to the bath-based clarification processes, a dispenser-based clarification approach uses substantially smaller volumes of clarification reagents. As the reagents are potentially hazardous and expensive, the substantially smaller volumes enables cost savings and decreases the waste-burden of the process. Clarifying samples from pigment obfuscation has seen a manual process using baths of potentially dangerous chemicals. Studies that present proposed solutions to clarifying samples typically recite the "bleaching" composition, conditions, and the effect of the bleaching on sample integrity. By design, the "bleaching" process is intended to degrade melanin polymers. While degradation of the melanin polymers results in decreased obfuscation, concomitant degradation to the tissue may render the sample unusable. A sample may not be usable if the "bleaching" process leaves the sample morphologically degraded and/or the antigenic/genetic markers therein destroyed or denatured.

One aspect of the present disclosure is that the methods, kits, and systems described herein are non-damaging to the sample, wherein non-damaging means that the sample is morphologically readable and the antigenic/genetic characteristics of the sample remain expressed. In one embodiment, the method includes applying a second clarifying reagent so that the second clarifying reagent contacts the sample subsequent to applying the first clarifying reagent and prior to applying the chromogenic reagent. In another embodiment, the method includes applying a third or further clarifying reagent so that the additional clarifying reagent contacts the sample subsequent to applying the clarifying reagent and prior to applying the chromogenic reagent. In one embodiment, the method includes monitoring the sample for clarification and repeating the application of clarifying reagent until the sample is adequately clarified. The monitoring means may include digital microscopy coupled with image analysis or other solutions known in the art.

Manual methods require technicians directly handling and preparing the chemical mixtures in relatively large volumes (e.g. routinely 20 mL or more). Various compositions have been used, the primary selections being hydrogen peroxide and permanganate solutions. Various additives, accelerants, and conditions have been implemented in attempts to improve the process; however, an efficient automated process is an unmet need. One aspect of the present invention is that the processes do not require submersion of samples in baths, that is, embodiments of the methods, systems, and kits are bath-free.

In one embodiment, applying the clarifying reagent includes applying vortex mixing (see U.S. Pat. No. 7,404,927, which is hereby incorporated by reference in its entirety for disclosure related to vortex mixing) or platen assembly mixing (e.g. "Floatable opposables for applying fluids to process biological samples, U.S. Published Application No. 2011/0305842, which is hereby incorporated by reference for disclosure related to platen assembly mixing) to agitate the clarifying reagent while in contact with the sample. Agitation of the clarifying reagent while it is in contact with the sample enhances the rate of the clarification and enhances the homogeneity of the solution over the sample, thus leading to more uniform clarification. Agitation also enables the more complete consumption of the clarifying reagents so that the waste-stream from the automated instrument includes reagents whose reactivity is substantially expended. Automated implementation of the method provides capability and reproducibility resulting in superior performance in comparison to the manual process. In one embodiment, applying the clarifying reagent includes applying drops of the clarifying reagent onto the sample or applying drops of the clarifying reagent in the vicinity of the sample and forcing the drops to contact with the sample in a turbulent flow regime. Turbulent flow regimes provide improved mixing in contrast to laminar flow regimes. Vortex mixing and platen assembly mixing are capable of producing turbulent flow regimes.

In illustrative embodiments, the method includes applying a chromogenic reagent so that the sample is specifically stained. In one embodiment, specifically staining includes the application of a primary stain that selectively stains portions of the sample through adhesion associated with hydrophobicity, intercalation, or other non-recognition associations. For example, hematoxylin and eosin staining (H&E staining) is well known in the art. Reference is made to U.S. Published Patent Application 2008/0227143, which is hereby incorporated by reference for disclosure related to hematoxylin and primary staining. H&E staining is used for the evaluation of cellular morphology and is the primary tool for pathologically diagnosing cancer.

In further illustrative embodiments, the method includes applying an immunohistochemical (IHC) binding reagent or an in situ hybridization (ISH) binding reagent so that the IHC binding reagent or the ISH binding reagent contact the sample. ISH can be used to diagnose the presence of a genetic abnormality or condition. For example, ISH may be used to detect gene amplification, deletion, or translocation of genes related to a particular disease. ISH is also useful in the diagnosis of infectious diseases as it allows detection of microbial and viral sequences within infected cells. IHC includes antibodies specifically binding epitopes of interest. The epitopes, also referred to as antigens or antigenic sequences, are portions of proteins that have been established as a marker of clinical interest. For example, the epitope may be a mutated form of a protein, a protein-protein binding site, or a normal protein that is expressed at a concentration either higher or lower than normal, such as in a control sample. Detection and/or quantification of epitopes in various biological samples have been used for a vast number of clinical purposes.

Both IHC and ISH involve a specific recognition event between a nucleic acid probe (ISH) or an antibody (IHC) and a target within the sample. This specific interaction labels the target. The label can be directly visualized (direct labeling) or indirectly observed using additional detection chemistries. Chromogenic detection, which involves the deposition of a chromogenic substance in the vicinity of the label, involves further detection steps to amplify the intensity of the signal to facilitate visualization. Visualization of the amplified signal (e.g. the use of reporter molecules) allows an observer to localize targets in the sample.

Chromogenic detection offers a simple and cost-effective method of detection. Chromogenic substrates have traditionally functioned by precipitating when acted on by the appropriate enzyme. That is, the traditional chromogenic substance is converted from a soluble reagent into an insoluble, colored precipitate upon contacting the enzyme. The resulting colored precipitate requires no special equipment for processing or visualizing. Table 1 is a non-exhaustive list of chromogen systems useful within the scope of the present disclosure:

TABLE 1

Chromogenic detection reagents.

| Abbr. | Name | Color | Enzyme |
|---|---|---|---|
| DAB | 3,3'-diamino-benzidine + $H_2O_2$ | brown - black | peroxidase |
| AEC | 3-amino-9-ethyl-carbazole + $H_2O_2$ | red | peroxidase |
| CN | 4-chloro-1-naphthol + $H_2O_2$ | blue | peroxidase |
| BCIP/ NBT | 5-bromo-4-chloro-3-indolyl-phosphate + nitroblue tetrazolium | indigo - black | alkaline phosphatase |
| FAST RED | 4-chloro-2-methylbenzenediazonium + 3-hydroxy-2-naphthoic acid 2,4-dimethylanilide phosphate | red | alkaline phosphatase |
| FAST BLUE | Naphthol AS-MX phosphate disodium salt + fast blue BB salt hemi(zinc chloride) salt | blue | alkaline phosphatase |
| FUCH-SIN | Naphthol AS-BI + New Fuchsin | red | alkaline phosphatase |
| NBT | nitroblue tetrazolium + phenazine methosulfate | blue - purple | dehydrogenase |
| ALK GOLD† | 3-methyl-1-phenyl-1H-pyrazol-5-yl dihydrogen phosphate + fast blue BB | yellow - gold | alkaline phosphatase |

Table 1, while not exhaustive, provides insight into the varieties of presently available chromogenic substances (†WO2012/024185, Kelly et al. "Substrates for Chromogenic detection and methods of use in detection assays and kits").

Referring now to FIG. 1(A)-1(D), shown are photomicrographs of serial microtome sections of a sample (melanoma tissue sample), wherein 1(A) shows obfuscations associated with pigments within the sample. The photomicrograph shows lightly stained cells containing darkly stained (blue) nuclei (as exemplarily indicated with an arrow marked with "N"). Dark bodies (brown) are also evident within the photomicrograph (as exemplarily indicated with an arrow marked with "M"). These dark bodies are melanin. The unclarified melanoma section was stained with an illustrative IHC protocol except that a primary antibody was not included. Thus, the photomicrograph shows the background level of pigment present in the sample without specific staining. FIG. 1(B) shows a serial section of the same sample specifically stained with DAB. The melanoma case was stained with an illustrative IHC protocol using an antibody to a cytoplasmically expressed cancer marker. Representative melanoma markers include MART-1/melan A (A103) Product No. 790-2990; S100 (4C4.9) Product No. 790-2914; Melanosome (HMB45) Product No. 790-4366; MITF (C5/D5) Product No. 790-4367; Tyrosinase (T311) Product No. 790-4365; or NGFR (MRQ-21) Product No. 760-4391, all available from Ventana Medical Systems Inc., Tucson, Ariz. FIG. 1(B) shows the obscuring nature of the melanin pigment in relation to the specific DAB staining when no clarification is performed, which can hinder identification and scoring of the specific staining. The DAB staining results in a brown signal associated with the cellular marker distribution. The melanin can be seen as the dark bodies evident within the photograph. The signal associated with the specific staining is similar in color to the melanin deposits and precise distinction between the chromogenic signal and the melanin deposits is difficult. Accordingly, FIG. 1(B) is exemplary of specific staining obfuscation by endogenous pigments. FIG. 1(C) shows a serial section of the sample treated with a clarifying reagent. While the sample was stained with hematoxylin, it was not specifically stained using IHC or ISH. As such, there is no signal associated with a cancer marker. The sample underwent a representative clarification process at 55° C. for 2 hours with 3% $H_2O_2$ followed by staining with a mock IHC protocol lacking a primary antibody. This photomicrograph shows that heavily pigmented melanomas can be clarified completely using this procedure. Obtaining complete clarification of a sample is important for accurately interpreting the subsequent IHC staining. FIG. 1(C) shows an exemplary sample clarified by the methods described herein to decolorize a highly pigmented sample. It is evident that the clarifying procedure removed obfuscation associated with the pigment and cellular morphology is preserved across the sample. FIG. 1(D) shows a serial section of the sample treated with the clarifying reagent and specifically stained with DAB. The specific staining from the DAB is clear and not obscured by melanin in contrast to the photomicrograph shown FIG. 1(B). The lack of obfuscating pigments provides a qualified reader an advantage in accurately and confidently deriving medical value from the assay since the dark bodies associated with the melanin do not obscure the specific staining. FIG. 1(D) shows a serial section of the melanoma case that underwent clarification at 55° C. for 2 hours with 3% $H_2O_2$ and was subsequently stained with an IHC protocol using an antibody to a cytoplasmic protein visualized with DAB. The photomicrograph shows the ability of the clarification procedure to remove obscuring melanin pigment, allowing for the antibody-specific staining to be unambiguously identified and quantitated.

Referring now to FIG. 2(A)-2(D), shown are photomicrographs of serial microtome sections of a different melanoma tissue sample showing sections 2(A) not clarified and not stained with IHC, 2(B) not clarified but stained with IHC, 2(C) clarified but not stained with IHC, and 2(D) clarified and stained with IHC. Each FIG. 2(A)-2(D) are stained with hematoxylin to reveal cellular morphology.

Figure 2B:
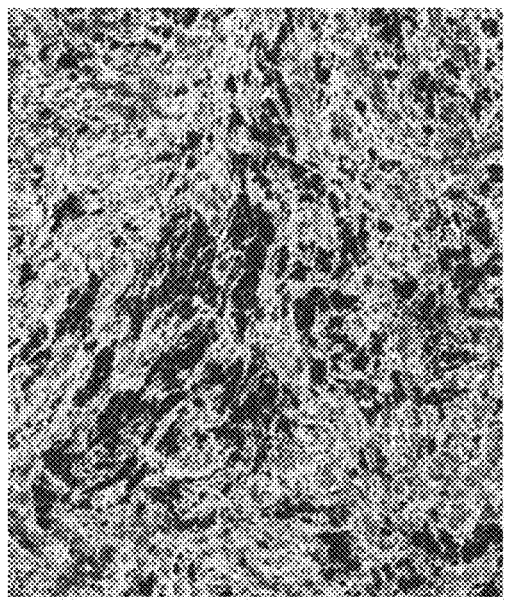
Figure 2C:
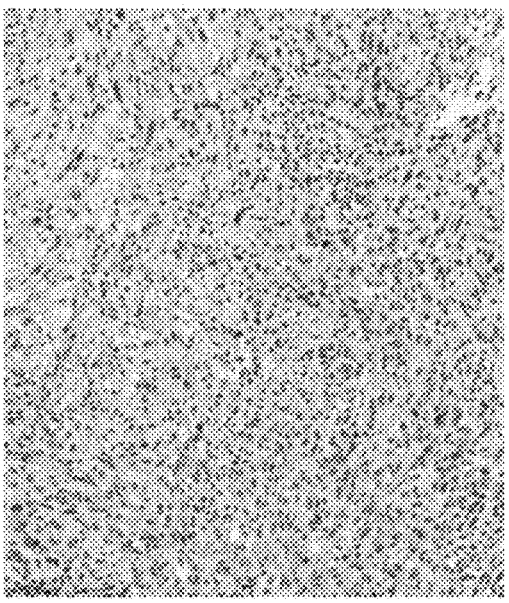
Figure 2D:
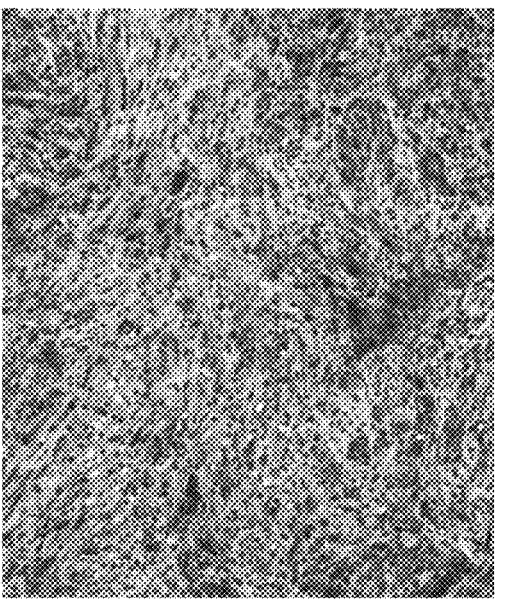

One aspect of FIG. 2(A)-(D) is that they show clarification of a heavily pigmented and heavily obscuring melanoma using a fully automated clarification protocol. Serial sections of the melanoma case were treated. FIG. 2(A) shows the unclarified melanoma section stained with a mock IHC protocol lacking a primary antibody. This photomicrograph illustrates the background level of pigment present in the sample. FIG. 2(B) shows a serial section of the melanoma case stained with the IHC protocol using an antibody to a cytoplasmically expressed cancer marker and visualized with DAB. The photomicrograph shows the obscuring nature of the melanin pigment in relation to the specific DAB staining when no clarification is performed, which can hinder identification and scoring of the specific staining. FIG. 2(C) shows a serial section of the melanoma case that underwent clarification at 60° C. for 1 hour with 9% $H_2O_2$ followed by staining with a mock IHC protocol lacking a primary antibody. FIG. 2(D) shows a serial section of the melanoma case that underwent clarification at 60° C. for 1 hour with 9% $H_2O_2$ and was subsequently stained with an IHC protocol using an antibody to a cytoplasmic protein and visualized with DAB.

FIGS. 2 (A)-2(D) show the ability of the clarification procedure to remove obscuring melanin pigment, allowing for the antibody-specific staining to be unambiguously identified and quantitated. Without clarification, interpretation of specific staining is difficult when obfuscating pigments are present. In particular, the appearance of FIG. 2(A) and FIG. 2(B) are difficult to distinguish. A pathologist reading FIG. 2(B) would have difficulty assessing whether specific staining was present, and if present, to assess a staining signal intensity of 1, 2, 3 or 4. FIG. 2(C), which could be used as a control to the specific staining shown in FIG. 2(D), shows that the sample can be clarified and that the morphology of the sample remains intact. FIG. 2(D), with the use of FIG. 2(C) as a control, shows specific staining that is readily interpretable by a qualified reader. The pigments, having been rendered non-obfuscating, do not impede the interpretation of the sample by a qualified reader.

Figure 3A:
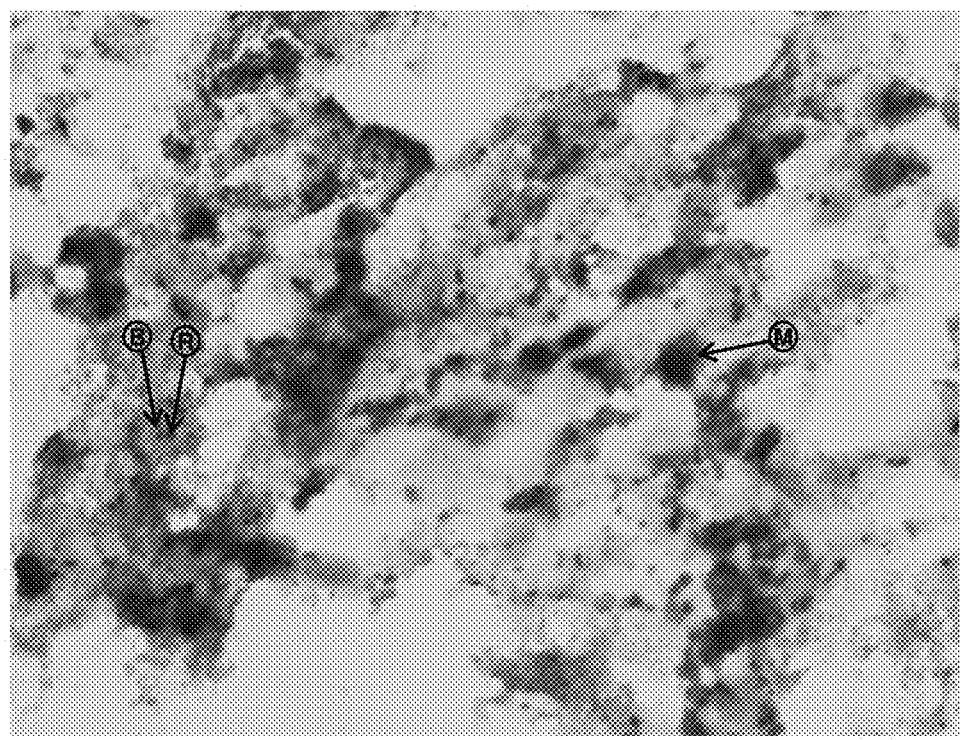
FIG. 3(A)-3(B) are photomicrographs of serial microtome sections of a different melanoma tissue sample showing an in situ hybridization (ISH) signal, wherein (A) includes obfuscations associated with pigments within the sample, the sample being darkly pigmented with melanin and (B) shows the sample treated with the clarifying reagent providing enhanced visibility of the ISH signal.
Figure 3B:
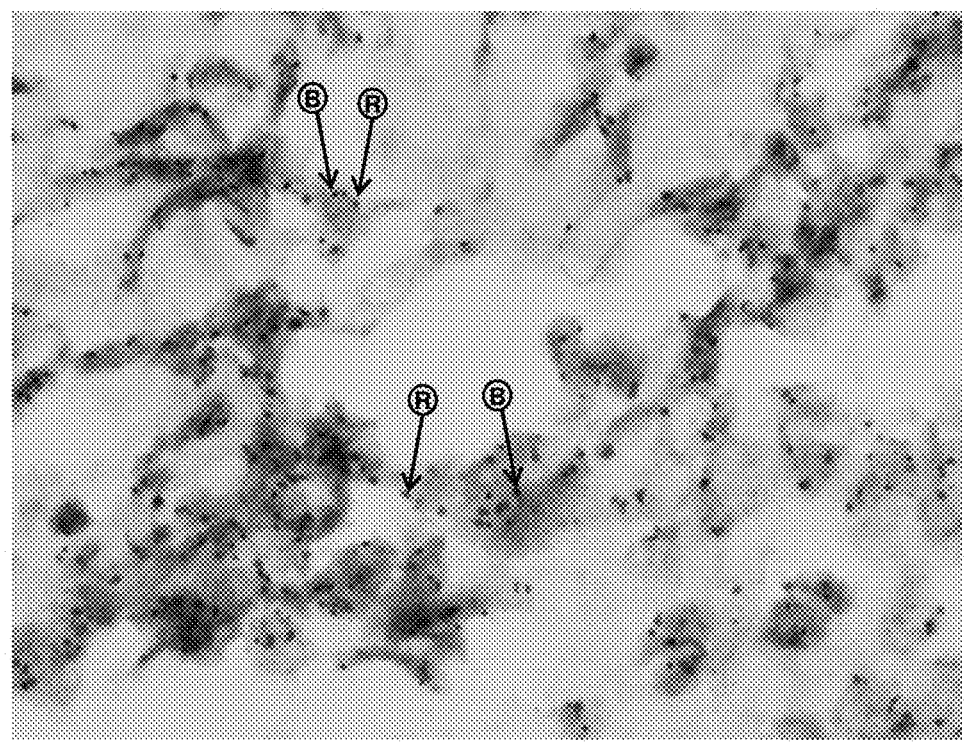

FIG. 3(A)-3(B) are photomicrographs of serial microtome sections of a melanoma tissue sample, 3(A) shows obfuscations of ISH signals by melanin pigments and 3(B) shows ISH signals clarified through processes described herein. Both 3(A) and 3(B) show ISH signals for copy number (e.g. amplification) probes which provide a chromogenic spot for every copy of a particular sequence. Amplifications are typically read by assessing the ratio of number of spots associated to the target to the number of spots associated with a centromere control within a particular cell (for further explanation reference is made to WO2011/133625, which is hereby incorporated by reference in its entirety for disclosure related to two-color chromogenic ISH). As such, this type of ISH signal is read by counting the discrete signals using a binary approach (e.g. the signal is counted or not). Furthermore, the exemplary photomicrographs 3(A) and 3(B) show ISH signals detected using Fast Red (red) (as exemplarily indicated with arrows marked with "R") and elemental silver (black) (as exemplarily indicated with arrows marked with "B"). Accordingly, the ISH signal is binary and colorimetrically distinct from the melanin pigment that appears brown (as exemplarily indicated with an arrow marked with "M"). However, even under these conditions, FIGS. 3(A) and 3(B) show the resultant advantage of clarifying the sample using processes disclosed herein as ISH signals in 3(B) are interpretable while ISH signals within 3(A) are obscured.

FIG. 3(A)-3(B) shows that the application of the clarification protocol to ISH. FIG. 3(A) shows an unclarified, heavily pigmented melanoma case stained for PIK3CA (black signals) and Chromosome 3 (red signals). In the few unpigmented cells both the gene and chromosome signals can be readily seen. However, in the pigmented cells the gene and chromosome signals are obscured. FIG. 3(B) shows a serial section clarified and stained for PIK3CA (black signals) (as exemplarily indicated with arrows marked with "B") and Chromosome 3 (red signals) (as exemplarily indicated with arrows marked with "R"). The clarification procedure removes all of the pigment from the cells allowing the underlying gene and chromosome signals to be seen and enumerated. According to another aspect, FIG. 3(A)-3(B) show that melanoma samples that may not be scorable under standard ISH conditions can be scored using a staining procedure that includes a clarification process.

Figure 4:
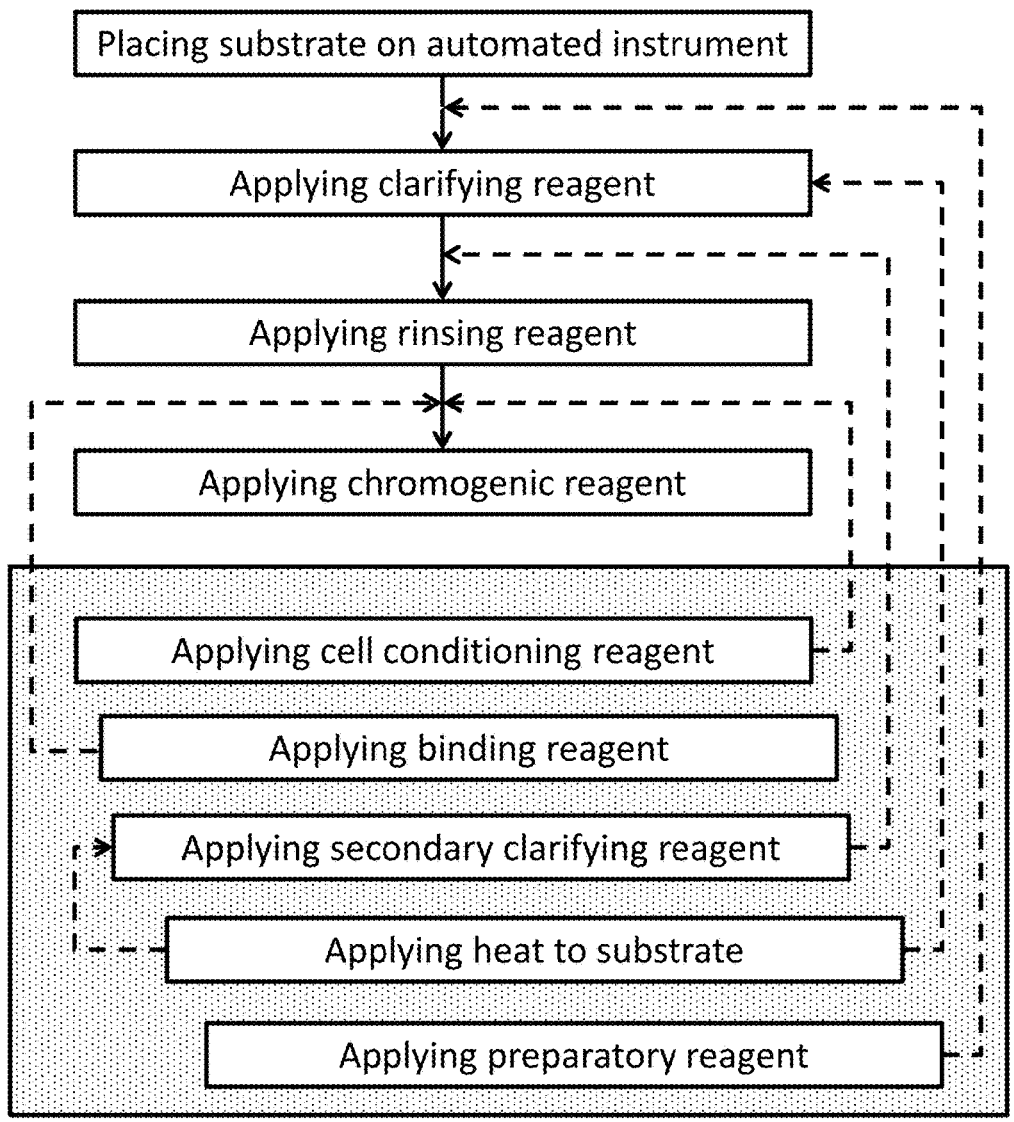
FIG. 4 shows a diagram representing a method according to one embodiment of the present invention, further showing steps which, if incorporated form further embodiments.

Referring now to FIG. 4, a diagram showing an illustrative embodiment of the present disclosure including placing a substrate on an automated instrument, applying a clarifying reagent, applying a rinsing reagent, and applying a chromogenic reagent is disclosed. FIG. 4 includes solid arrows that indicate a proposed order of steps beginning at placing the substrate on the automated instrument. Below and in a shaded box are steps which may be included in processes according to various embodiments of the disclosed method. The dashed arrows indicate when the steps may be introduced so as to establish further embodiments. Dashed arrows directed towards solid arrows indicate that the additional step is intended to occur between the two steps the solid arrow connects. Dashed arrows directed towards boxes indicate that the additional step occurs during or concurrently with the process step within the box.

Referring again to FIG. 4, a method according to the present disclosure includes placing the substrate upon which the sample is affixed in or on the automated instrument. In one embodiment, a preparatory reagent can be applied. Illustratively, the method includes applying a deparaffinization reagent to remove paraffin. U.S. Patent Publications Nos. 2006/0252025 and 2008/0261266, which are incorporated by reference herein for disclosure related to deparaffinization, disclose methods and compositions that are illustrative of embodying methods described herein. Exemplary deparaffinization solutions are available from Ventana Medical Systems, Inc., Tucson, Ariz. (EZ Prep (10×) catalog #: 950-102).

In another embodiment, the method includes applying a buffered preparatory solution so that the buffered preparatory solution contacts the sample prior to applying the clarifying reagent. In one embodiment, a composition of buffer is used that matches the clarifying reagent except for the inclusion of an oxidizing agent. The preparatory solution may be used with an attendent increase in temperature prior to applying the clarifying reagent. The preparatory solution may also serve to modify the osmolality of the sample prior to adding the clarifying reagent. The preparatory solution may also serve as a wash for reagents associated with deparaffinization or other steps that may have occurred prior to placing the substrate on the automated instrument.

Difficulties frequently encountered in both IHC and ISH testing results from the manner in which the tissues are typically preserved. The mainstay of the diagnostic pathology laboratory has been for many decades the formalin-fixed, paraffin-embedded block of tissue, sectioned and mounted upon glass slides. Fixation in such a preservative causes cross-linking of macromolecules, both amino acids and nucleic acids. These cross-linked components must be removed to allow access of the probe to the target nucleic acid and to allow the antibody to recognize the corresponding antigen. "Unmasking" the antigen and/or nucleic acid is typically accomplished manually with multiple pretreatment, proteolytic digestion, and wash steps. Prior to clarifying or staining, complete removal of the paraffin is also required so that it does not interfere with antibody or probe binding. Deparaffinization may be achieved by the use of multiple (e.g. two or three) successive clearing reagents that are paraffin solvents (e.g. xylene, xylene substitutes, or toluene).

In an illustrative embodiment, a method of clarifying includes the step of cell conditioning. Cell conditioning is discussed in greater detail in U.S. Pat. No. 6,855,552, Towne, et al. "Automated immunohistochemical and in situ hybridization assay formulations", the subject matter of which is expressly incorporated by reference. In illustrative cell conditioning steps, a cell conditioning reagent is applied and the sample is contacted at the appropriate temperature for an appropriate duration of time so that the antigens and/or nucleic acid targets are sufficiently expressed for detection. One aspect of the present disclosure is that the automated instrument can automatically adjust the cell conditioning duration and/or temperature in response to the clarification step. It was discovered that cell conditioning and clarifying steps have a cumulative effect on the sample that may warrant adjustment of the cell conditioning step in response to lengthy clarifying steps. One aspect of the system is that lengthy clarification steps can be programmed within the microprocessor to automatically diminish the corresponding cell conditioning step so that tissue morphology is not adversely affected by the cumulative treatments. Cell conditioning may further include applying a protease reagent. Illustratively, a protease treatment may involve the step of contacting a protease solution to a biological sample. The protease treatment, as with cell conditioning, is intended to increase the expression of target antigens and/or nucleic acids. In one embodiment, interpretable by the qualified reader includes the sample exhibiting antigenic and genetic characteristics consistent with or improved with respect to those of the sample prior to applying the clarifying reagent. In another embodiment, interpretable by the qualified reader includes the sample exhibiting antigenic and genetic characteristics consistent with or improved with respect to those of the sample prior to applying the clarifying reagent and the cell conditioning reagent.

Exemplary cell conditioning reagents include, for nucleic acid targets (ISH), a solution including ethylenediaminetetraacetic acid (EDTA) may be used. The contacting may be done at a temperature of about 95° C. for between about 2 and about 90 minutes. For protein targets (IHC), a cell conditioning solution may be a boric acid buffer. The contacting may be may be done at a temperature of about 100° C. for between about 2 and about 90 minutes. A partial list of possible reagents appears in Analytical Morphology, Gu, ed., Eaton Publishing Co. (1997) at pp. 1-40. Sodium dodecyl sulfate (SDS) and/or ethylene glycol may be included in the conditioning solution. Furthermore, metal ions or other materials may be added to these reagents to increase effectiveness of the cell conditioning. Exemplary cell conditioning solutions are available from Ventana Medical Systems, Inc., Tucson, Ariz. (Cell Conditioning 1 (CC1) catalog #: 950-124; Cell Conditioning 2 (CC2) catalog #: 950-123; SSC (10×) catalog #: 950-110; ULTRA Cell Conditioning (ULTRA CC1) catalog #: 950-224; ULTRA Cell Conditioning (ULTRA CC2) catalog #: 950-223, Protease 1 catalog #: 760-2018; Protease 2 catalog #: 760-2019; Protease 3 catalog #: 760-2020). In one embodiment, applying the immunohistochemical binding reagent or the in situ hybridization binding reagent occurs subsequent to applying the cell conditioning reagent and prior to applying the chromogenic reagent.

In illustrative embodiments, the method includes applying a rinsing reagent. Between various steps described herein and as part of the system described herein, rinse steps may be added to remove unreacted residual reagents from the prior step. Rinse steps may further include incubations which include maintaining a rinsing reagent on the sample for a pre-determined time at a pre-determined temperature with or without mixing. The conditions appropriate for the rinsing steps may be distinct between the various steps. Exemplary rinsing reagents are available from Ventana Medical Systems, Inc., Tucson, Ariz. (Reaction Buffer (10×) catalog #: 950-300; Special Stains Wash (10×) catalog #860-015:).

In illustrative embodiments, a kit for decolorizing obfuscating pigments in a sample includes a reagent bottle and a clarifying reagent deposited in the reagent bottle. The clarifying reagent comprises hydrogen peroxide and an aqueous solution and the reagent bottle is configured to be operably connected to an automated slide staining apparatus such that the automated slide staining apparatus controls the application of the clarifying reagent so that the clarifying reagent contacts the sample. In one embodiment, the reagent bottle is a dispenser for an automated instrument (e.g., U.S. Pat. Nos. 5,232,664 and 6,537,818, hereby incorporated by reference for disclosure related to systems and methods of dispensing liquids).

In illustrative embodiments, a system for alleviating specific signal obfuscation for a histopathological sample containing pigments includes an automated instrument, a clarifying reagent, and a chromogenic reagent. The automated instrument is configured to receive the histopathological sample adhered to a substrate, to deliver the clarifying reagent and the chromogenic reagent to the sample, and to provide heating and mixing to the clarifying reagent and the chromogenic reagent delivered to the sample, the clarifying reagent is configured to contact the histopathological sample and render the obfuscating pigments decolorized, and the chromogenic reagent is configured to contact the histopatholigical sample and deposit a specific signal. In one embodiment, the automated instrument is an automated slide staining instrument and the substrate is a microscope slide, the automated slide staining instrument being configured to receive the microscope slide. In another embodiment, the automated slide staining instrument includes a heated slide platform upon which the microscope slide is positioned, the heated slide platform being configured to evenly heat the microscope slide, the heat transferred to the microscope slide being transferred to the sample. In another embodiment, the automated instrument is configured to apply washing reagents to the sample. In yet another embodiment, the system is devoid of a bath for submersion of the sample. Exemplary automated systems available through Ventana Medical Systems, Inc., Tucson, Ariz. include SYMPHONY® Staining System, catalog #: 900-SYM3, VENTANA® BenchMark Automated Slide Preparation Systems, catalog #s: N750-BMKXT-FS, N750-BMKU-FS, VENTANA, and VENTANA® BenchMark Special Stains automated slide stainer. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

Illustrative instrumentation systems are designed to sequentially apply reagents to tissue sections mounted on one by three inch glass microscope slides under controlled environmental conditions. The instrument must perform several basic functions such as reagent application, washing (to remove a previously applied reagent), jet draining (a technique to reduce the residual buffer volume on a slide subsequent to washing), application of a light oil used to contain reagents and prevent evaporation, and other instrument functions. Exemplary staining instruments process slides on a rotating carousel. The slides maintain a stationary position and a dispenser carousel rotates the reagents above the fixed slides. The processes described herein can be performed using various physical configurations. The process of clarifying and staining tissue on a slide consists of the sequential repetition of basic instrument functions described above. Essentially a reagent is applied to the tissue then incubated for a specified time at a specific temperature. When the incubation time is completed the reagent is washed off the slide and the next reagent is applied, incubated, and washed off, etc., until all of the reagents have been applied and the staining process is complete.

For related disclosure, reference is made to Richards et al. U.S. Pat. No. 6,296,809, assigned to Ventana Medical Systems, which describes an apparatus and methods for automatically staining or treating multiple tissue samples mounted on microscope slides so that each sample can receive an individualized staining or treatment protocol even when such protocols require different temperature parameters. More specifically, described is an apparatus comprising a computer controlled, bar code driven, staining instrument that automatically applies chemical and biological reagents to tissue or cells mounted or affixed to standard glass microscope slides. A plurality of slides are mounted in a circular array on a carousel which rotates, as directed by the computer, to a dispensing location placing each slide under one of a series of reagent dispensers on a second rotating carousel positioned above the slides. Each slide receives the selected reagents (e.g. DNA probe) and is washed, mixed, and/or heated in an optimum sequence and for the required period of time.

In one embodiment, the sample is a tissue or cytology sample mounted on a glass microscope slide. In one embodiment, the glass microscope slide is configured to be compatible with an automated slide staining instrument. In another embodiment, the steps of clarifying a sample with pigment, contacting the sample with phosphate buffer, heating the sample to a predetermined temperature, contacting sample with hydrogen peroxide in phosphate buffer, and maintaining the sample step for a predetermined period of time at a predetermined temperature are performed by an automated instrument.

A mechanism by which hydrogen peroxide clarifies melanin is not fully understood. Without being bound to any particular theory, it is presently understood that a peroxide can oxidize certain radicals (such as the chromogenic group) on melanin molecules with or without disintegrating the melanin protein molecules. This may be important since the large amount of melano-protein molecules in the cytoplasm may affect the accessibility of an antibody to a nuclear antigen such as Ki67. As such, in some embodiments, there is an advantage to applying a clarification reagent prior to applying the binding reagent. The formation of hydroxyl radicals during melanin decolorization has been reported on the basis of the electrochemical detection of hydroxylation products of salicylate used as hydroxide scavengers. Redox conversion of bound-to-melanin copper ions was reported by EPR spectroscopy and the direct measurement of melanin-Cu(II) complexes. It has also been reported that melanin-copper(I) complexes were oxidized by either oxygen or hydrogen peroxide. According to our own understanding and that information reported, decolorizing melanin is likely a complex process with two distinct stages, reversible oxidation of the hydroquinone moieties of melanin followed by irreversible reactions of the monomers that lead to degradation of the melanin polymer.

While the present application describes, in particularity, methods of clarifying a sample having pigments therein, the approaches described herein are general and applicable to various biological samples including pigments. The application of the disclosed technology to biological samples with different types of pigments is within the scope of the present application. By so applying the disclosed technology, the present method enables the enhanced visualization of cell morphology and staining procedures such as hematoxylin and eosin, IHC, or ISH. Enhanced visualization improves determination of disease states and development of improved predictive and prognostic analyses of biological samples for patients.

Furthermore, the application of the disclosed technology by clarifying may utilize various chemicals which remove color typically by oxidation, such as peroxides including hydrogen peroxide. Additional oxidizers such as chlorine based substances including sodium hypochlorite are within the scope of the present application. Reducing substances are also within the scope of the present application.

EXAMPLES

The following examples are provided to illustrate certain specific features of working embodiments and general protocols. The scope of the present invention is not limited to those features exemplified by the following examples.

IHC Procedure

The following protocols were implemented on a VENTANA® BenchMark XT (VMSI Catalog #: N750-BMKXT-FS) with NexES V10.6, the ranges providing illustrative process variations with the bracketed values representing an exemplary value:

(1) Baking may be performed to adhere tissue to slide especially for fresh cut slides; temperatures: 60° C.-75° C.; incubation time: 4-32 min; for online baking, set the temperature 2-4 degrees above the melting point of paraffin brand used, [No baking];

(2) Deparaffinization was performed to remove the wax for reagent penetration; the unique deparaffinization options include standard, extended and extended II; these procedures enable improved flexibility to allow greater success at optimizing difficult tissues; standard is the default and will reproduce the classic deparaffinization protocol using EZ Prep (VMSI Catalog #: 950-102); extended, when selected, will reproduce the deparaffinization from HER2 DDISH (VMSI Catalog #: 780-4422) (adding 5 extra EZ Prep rinsing steps to the standard protocol; extended II, when selected, will use LCS (VMSI Catalog #: 650-010), [Standard Deparaffinization, 75° C., 4 minutes; 3 EZ Prep rinses; 76° C., 4 minutes; Rinse];

(3) Pretreatment; on-slide post-fixation, option pretreatment, removal of excess protein (heat and enzyme); user-fillable fixative reagent; temperature from 37° C.-60° C.; user-fillable "FIXATIVE 1" through "FIXATIVE 10" incubation time from 4-32 min in Reaction Buffer; [No pretreatment];

(4) Cell Conditioning; used CC1 (VMSI Catalog #: 950-124), CC2 (VMSI Catalog #: 950-123) or Reaction Buffer (VMSI Catalog #: 950-300); CC1 with a slightly alkaline pH used for heat+buffer retrieval; CC2 pH of 6.0 used for heat+buffer retrieval, Reaction Buffer used for heat retrieval only; 1 to 5 cycles selectable; incubation times: 4-16 min; temperatures: 60° C.-100° C., [CC1 for 32 minutes-8 minutes at 95° C. followed by 24 minutes at 100° C.];

(5) Protease Treatment: cell conditioning using heat retrieval loosens crosslinks from fixation; protease "punches holes" in protein; combination may enable better sample penetration; enzyme choice and incubation time may be determined by reagent manufacturer, recommendation, experimentation, enzyme option; user-fillable dispensers to be used with ENZYME 1-10, pre-diluted Protease 1-3 (VMSI Catalog #s: 760-2018, 760-2019, 760-2020); pre-diluted ISH-Protease 1-3 (VMSI Catalog #s: 780-4147, 780-4148, 780-4149); incubation time from 4-32 min, [No protease used];

(6) Pre Primary Peroxidase Inhibit & Post Primary Peroxidase Inhibit (VMSI Catalog #: 253-4578); allows for inhibition of endogenous peroxidase after the primary has bound to the antigen; some antigens may be sensitive to hydrogen peroxide; this option can improve staining for those antibodies, [No Peroxidase Inhibition used];

(7) Apply rinsing reagent; Reaction Buffer; Apply LCS, [4 minutes, no heat];

(8) Clarification Process [described herein];

(9) Primary Antibody Application; primary antibody temperature and primary antibody dilution option; enables the user to modify the incubation temperature for the primary; adds an additional 900 µL of Reaction Buffer to the slide before primary antibody application; [anti-V600E (Clone VE1), Incubate 37° C. for 16 minutes];

(10) Detection links a "visual" molecule to the probe; UltraView or OptiView (VMSI Catalog #s: 760-500, 760-700) [OptiView]; and

(11) Counterstain & Post-counterstain; adds a "backdrop" color to the tissue; user can select from a list of counterstain reagents, including pre-dilute VENTANA reagents as well as user-fillable counterstain dispensers; incubation time is selectable from 4 min to 32 min; [counterstain 4 minutes with Hematoxylin II (VMSI Catalog #: 790-2208), Post-counterstain 4 minutes with Bluing Reagent (VMSI Catalog #: 760-2037)].

Exemplary Clarification Process (i) Heat slide to (37° C.-100° C.) [37° C.];
(ii) Jet drain [jet drain with Reaction Buffer];
(iii) Add aqueous solution (e.g. buffer) for equilibration [add 2 drops of 0.05M Sorensen's Phosphate Buffer pH 7.4];
(iv) Heat slide to selectable temperature (37° C.-100° C.) [55° C., 60° C., 65° C.];
(v) Jet drain [jet drain with Reaction Buffer];
(vi) Apply clarifying reagent [1-3 drops of 3-9% $H_2O_2$ in 0.05-0.1 M Sorensen's Phosphate Buffer pH 7.4;
(vii) Apply LCS;
(viii) Apply clarifying reagent [1-3 drops of 3-9% $H_2O_2$ in 0.05-0.1 M Sorensen's Phosphate Buffer pH 7.4;
(ix) Clarify for selectable time [4 min-1 hr 56 min];
(x) Apply rinsing reagent; [Reaction Buffer]. Repeat rinse step;
(xi) Jet drain slide;

ISH Protocol

The following protocols were implemented on a VENTANA® BenchMark XT with NexES V10.6, the ranges providing potential process variations with the bracketed values representing exemplary values:

(1) Baking; [No baking]
(2) Deparaffinization [Extended Depar, 72° C., cycles of 16, 12, 16, 12, 16 minutes; 4 rinse steps];
(3) Pretreatment; [No Pretreatment];
(4) Cell Conditioning; [CC2: 3 cycles of 12 minutes, 90° C.];
(5) Clarification Process [described herein];
(6) Protease Treatment [ISH-Protease 3 for 20 minutes, 37° C.];
(7) Clarification Process [described herein];
(8) Probe application [PIK3CA PCR probe (1041) plus Chromosome 3 centromeric probe (1041) plus HYB RDY SOL (VMSI catalog #780-4409) diluent (4040];
(9) Denaturation is used to unravel the strands of the target; probe denaturation temperatures: 60° C.-95° C.; incubation times: 4-32 min; increasing HybReady (which contains formamide) enables lower denaturation and hybridization temperatures, [80° C., 12 minutes];
(10) Hybridization allows the probe hybridize to the target; temperatures: 37° C.-60° C.; hybridization times: 1-12 hours; increasing HybReady (which contains formamide) enables lower denaturation and hybridization temperatures [44° C., 6 hours];
(11) Stringency washes are used to wash off the excess probe; user can choose to perform 3 stringency wash cycles, temperature and time are user selectable; first wash sets temperature condition for additional washes: 37° C.-95° C.; time for each cycle: 4-16 min, [3 washes, 72° C., 8 minutes];
(12) Detection, [ultraView SISH DNP Detection Kit (VMSI Catalog #: 760-098); ultraView Red ISH DIG Detection Kit (VMSI Catalog #: 760-505)]; and
(13) Counterstain; [counterstain 4 minutes with Hematoxylin II (VMSI Catalog #: 790-2208), Post-counterstain 4 minutes with Bluing Reagent (VMSI Catalog #: 760-2037)].

Exemplary variations in the protocol are described in the Tables 2-5.

TABLE 2

Figure 5A:
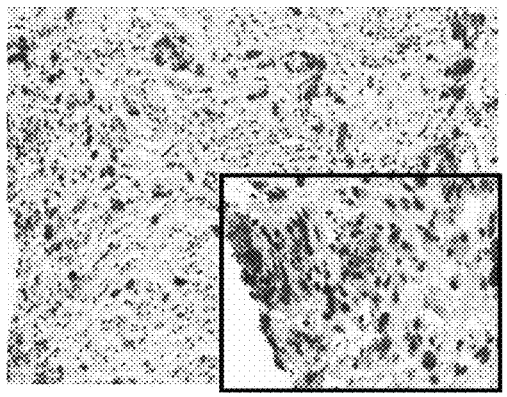
FIG. 5(A)-(E) are photomicrographs with inserts at higher magnifications of serial microtome sections of a melanoma tissue sample showing the effect of incubation time on clarification results under fixed temperature and peroxide conditions.
Figure 5B:
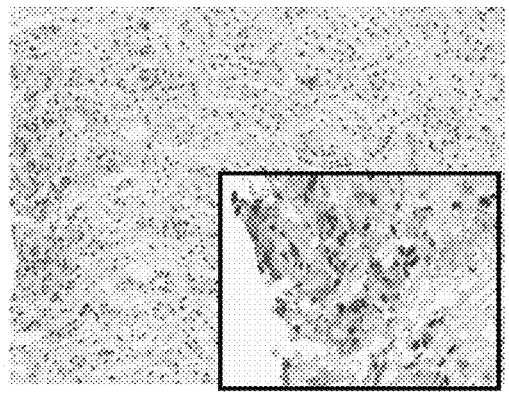
Figure 5C:
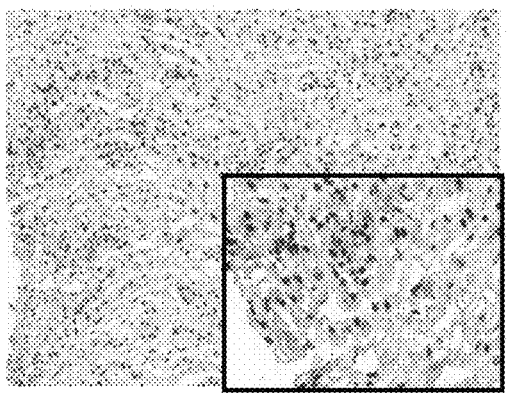
Figure 5D:
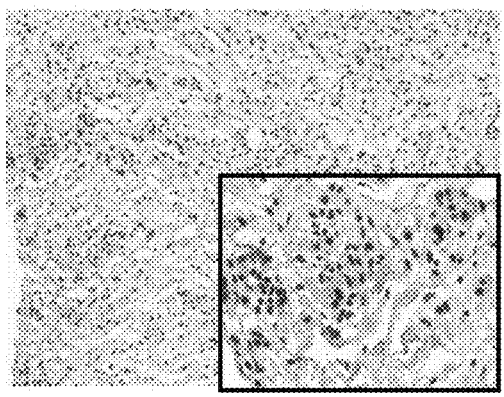
Figure 5E:
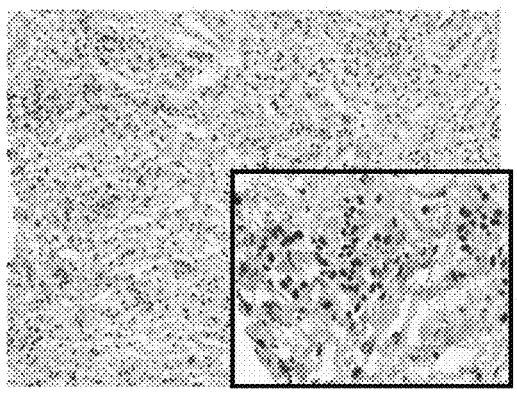
Figure 7A:
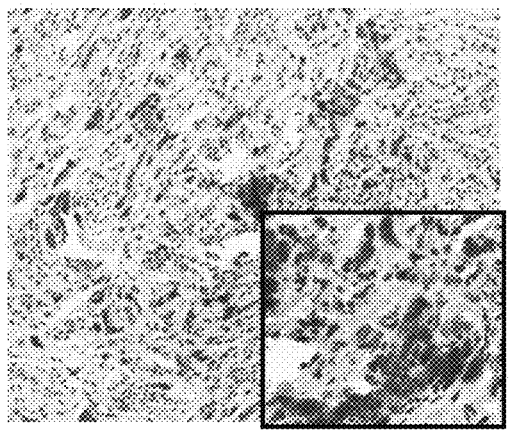
FIG. 7(A)-(E) are photomicrographs with inserts at higher magnifications of serial microtome sections of a melanoma tissue sample showing the effect of incubation time on clarification results using an increased concentration of peroxide.
Figure 7B:
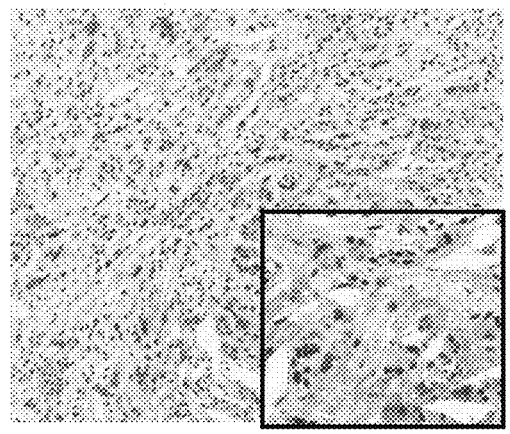
Figure 7C:
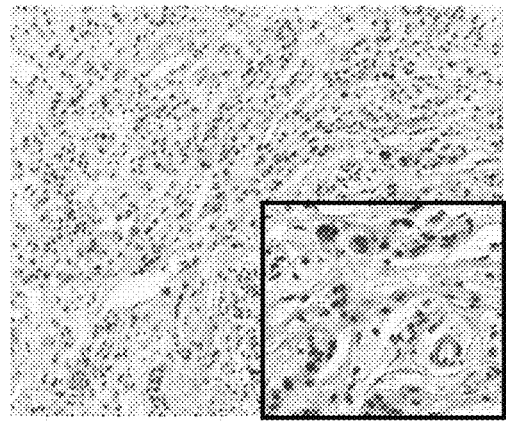
Figure 7D:
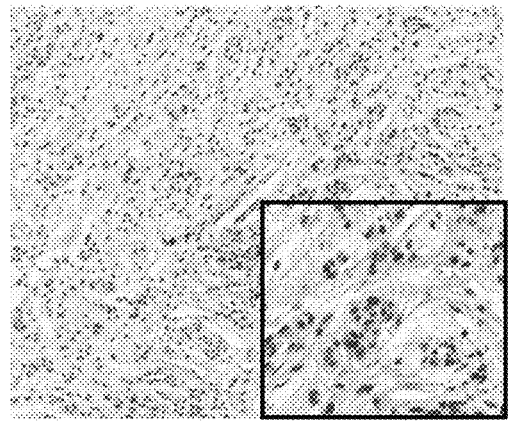
Figure 7E:
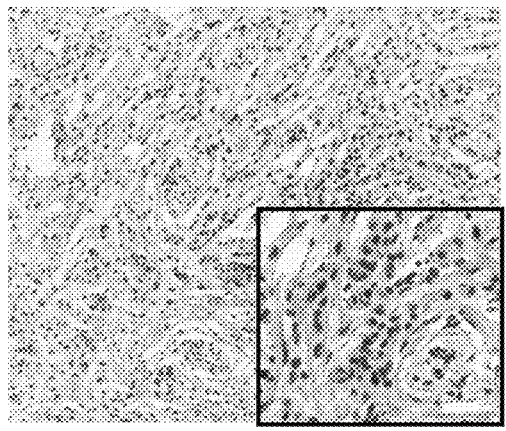

| Ex. # | Clarifying Step | Decolorization | Morphology | FIG. |
|---|---|---|---|---|
| 1 | No clarification step - control | None | Standard | FIG. 5(A) |
| 2 | 55° C. clarifying step with 3% H2O2 in 0.05M Sorensen's Phosphate Buffer pH 7.4 for 16 minutes | Incomplete | Maintained | FIG. 5(B) |
| 3 | 55° C. clarifying step with 3% H2O2 in 0.05M Sorensen's Phosphate Buffer pH 7.4 for 32 minutes | Nearly Complete | Maintained | FIG. 5(C) |
| 4 | 55° C. clarifying step with 3% H2O2 in 0.05M Sorensen's Phosphate Buffer pH 7.4 for 1 hour | Complete | Maintained | FIG. 5(D) |
| 5 | 55° C. clarifying step with 3% H2O2 in 0.05M Sorensen's Phosphate Buffer pH 7.4 for 2 hours | Complete | Maintained | FIG. 5(E) |
| 6 | No clarification step - control | None | Standard | FIG. 6(A) |
| 7 | 55° C. clarifying step with 3% H2O2 in 0.05M Sorensen's Phosphate Buffer pH 7.4 for 8 minutes | Incomplete | Maintained | FIG. 6(B) |
| 8 | 55° C. clarifying step with 3% H2O2 in 0.05M Sorensen's Phosphate Buffer pH 7.4 for 16 minutes | Incomplete | Maintained | FIG. 6(C) |
| 9 | 55° C. clarifying step with 3% H2O2 in 0.05M Sorensen's Phosphate Buffer pH 7.4 for 32 minutes | Nearly Complete | Maintained | FIG. 6(D) |
| 10 | 55° C. clarifying step with 3% H2O2 in 0.05M Sorensen's Phosphate Buffer pH 7.4 for 1 hour | Complete | Maintained | FIG. 6(E) |
| 11 | No clarification step - control | None | Standard | FIG. 7(A) |
| 12 | 55° C. clarifying step with 6% H2O2 in 0.05M Sorensen's Phosphate Buffer pH 7.4 for 8 minutes | Incomplete | Maintained | FIG. 7(B) |
| 13 | 55° C. clarifying step with 6% H2O2 in 0.05M Sorensen's Phosphate Buffer pH 7.4 for 16 minutes | Incomplete | Maintained | FIG. 7(C) |
| 14 | 55° C. clarifying step with 6% H2O2 in 0.05M Sorensen's Phosphate Buffer pH 7.4 for 32 minutes | Complete | Maintained | FIG. 7(D) |
| 15 | 55° C. clarifying step with 6% H2O2 in 0.05M Sorensen's Phosphate Buffer pH 7.4 for 1 hour | Complete | Maintained | FIG. 7(E) |

TABLE 3

Figure 8A:
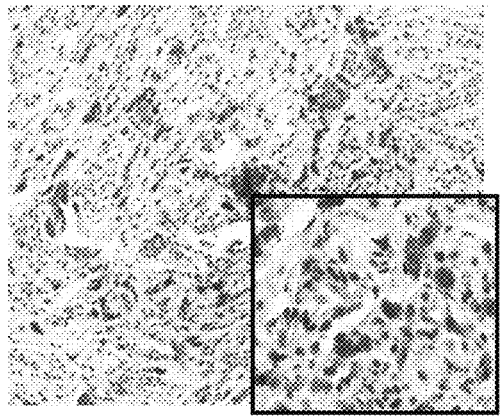
FIG. 8 (A)-(E) are photomicrographs with inserts at higher magnifications of serial microtome sections of a melanoma tissue sample showing the effect of incubation time on clarification results using a further increased concentration of peroxide.
Figure 8B:
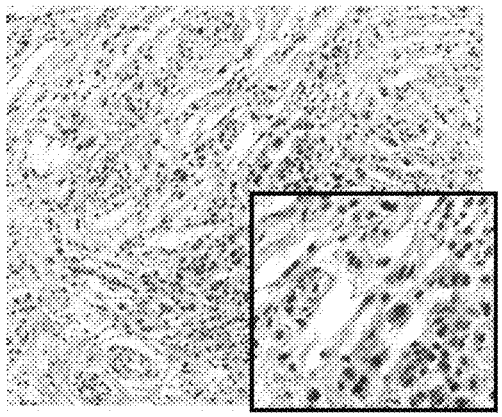
Figure 8C:
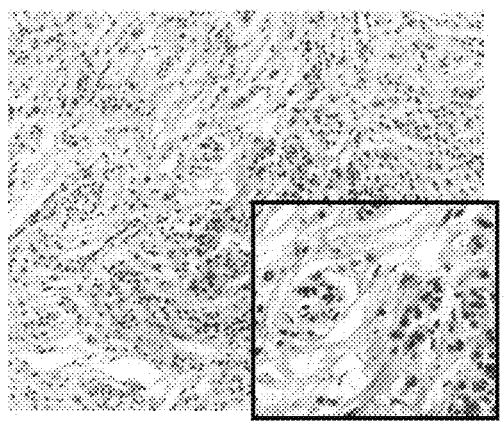
Figure 8D:
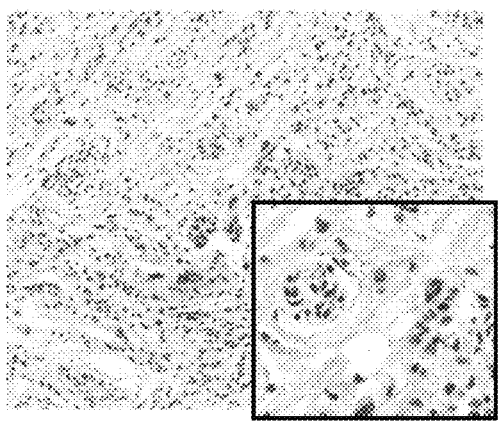
Figure 8E:
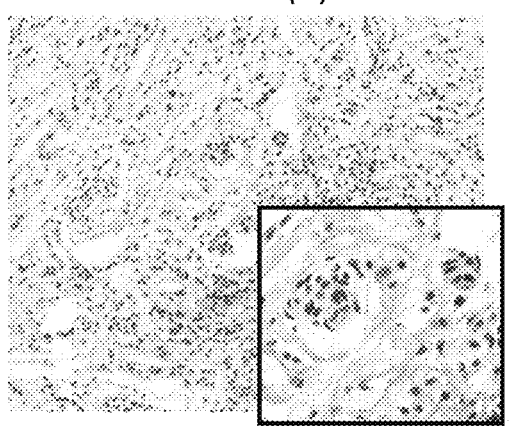
Figure 9A:
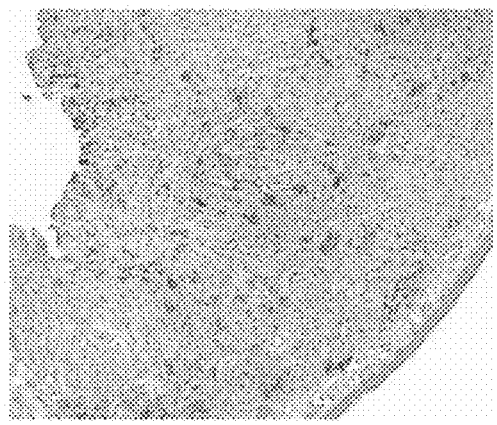
FIG. 9(A)-(F) are photomicrographs of serial microtome sections of a melanoma tissue sample showing the effect of reagent concentration on clarification results.
Figure 9B:
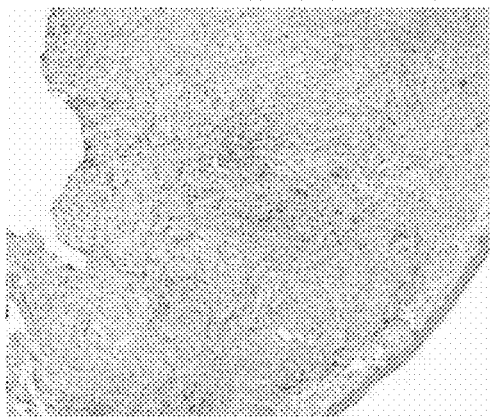
Figure 9C:
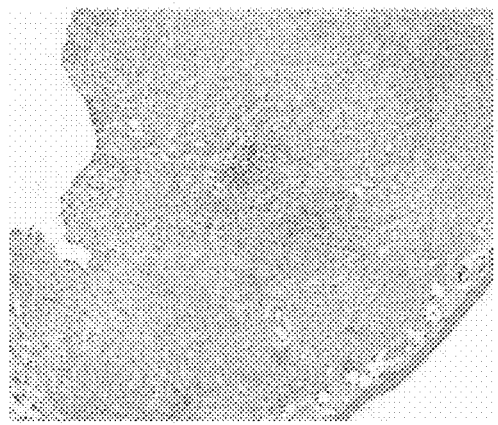
Figure 9D:
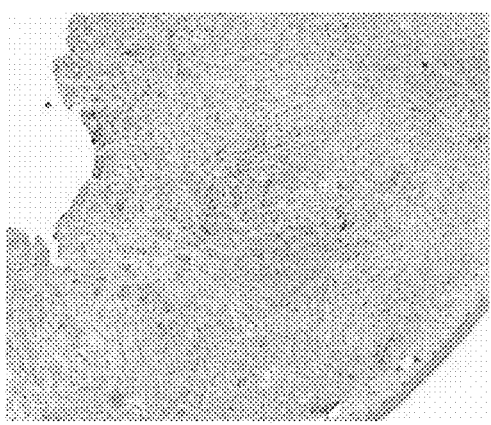

| Ex. # | Clarifying Step | Decolorization | Morphology | FIG. |
|---|---|---|---|---|
| 16 | No clarification step - control | None | Standard | FIG. 8(A) |
| 17 | 55° C. clarifying step with 9% H2O2 in 0.05M Sorensen's Phosphate Buffer pH 7.4 for 8 minutes | Incomplete | Maintained | FIG. 8(B) |
| 18 | 55° C. clarifying step with 9% H2O2 in 0.05M Sorensen's Phosphate Buffer pH 7.4 for 16 minutes | Incomplete | Maintained | FIG. 8(C) |
| 19 | 55° C. clarifying step with 9% H2O2 in 0.05M Sorensen's Phosphate Buffer pH 7.4 for 32 minutes | Complete | Maintained | FIG. 8(D) |
| 20 | 55° C. clarifying step with 9% H2O2 in 0.05M Sorensen's Phosphate Buffer pH 7.4 for 1 hour | Complete | Maintained | FIG. 8(E) |
| 21 | 55° C. clarifying step with 3% H2O2 in 0.05M Sorensen's Phosphate Buffer pH 7.4 for 8 minutes | Incomplete | Maintained | FIG. 9(A) |
| 22 | 55° C. clarifying step with 6% H2O2 in 0.05M Sorensen's Phosphate Buffer pH 7.4 for 8 minutes | Incomplete | Maintained | FIG. 9(B) |
| 23 | 55° C. clarifying step with 9% H2O2 in 0.05M Sorensen's Phosphate Buffer pH 7.4 for 8 minutes | Incomplete | Maintained | FIG. 9(C) |
| 24 | 55° C. clarifying step with 3% H2O2 in 0.05M Sorensen's Phosphate Buffer pH 7.4 for 16 | Incomplete | Maintained | FIG. 9(D) |

TABLE 3-continued

Figure 9E:
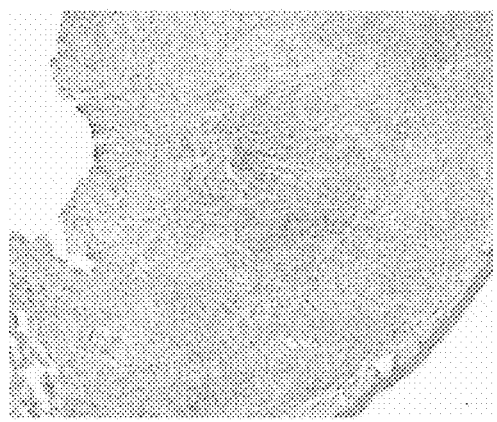
Figure 9F:

| Ex. # | Clarifying Step | Decolorization | Morphology | FIG. |
|---|---|---|---|---|
| 25 | 55° C. clarifying step with 6% H2O2 in 0.05M Sorensen's Phosphate Buffer pH 7.4 for 16 minutes | Nearly Complete | Maintained | FIG. 9(E) |
| 26 | 55° C. clarifying step with 9% H2O2 in 0.05M Sorensen's Phosphate Buffer pH 7.4 for 16 minutes | Nearly Complete | Maintained | FIG. 9(F) |

TABLE 4

Figure 10A:
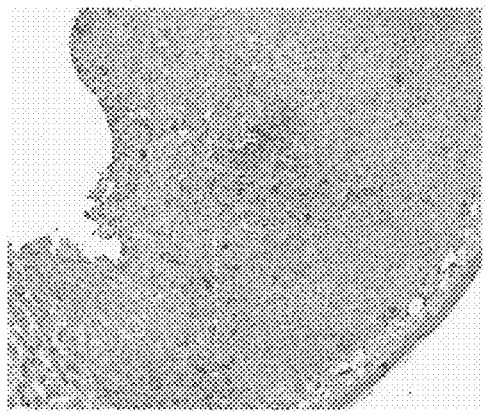
FIG. 10(A)-(F) are photomicrographs of serial microtome sections of a melanoma tissue sample showing the effect of reagent concentration and increased clarification temperature on clarification results.
Figure 10B:
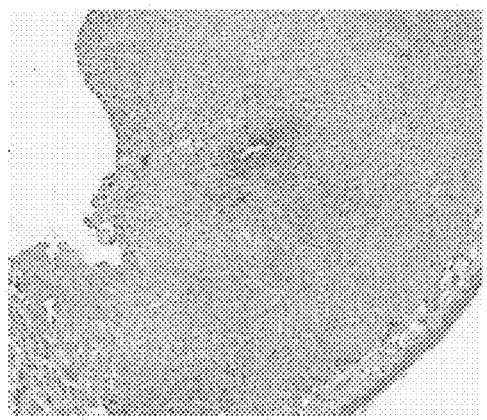
Figure 10C:
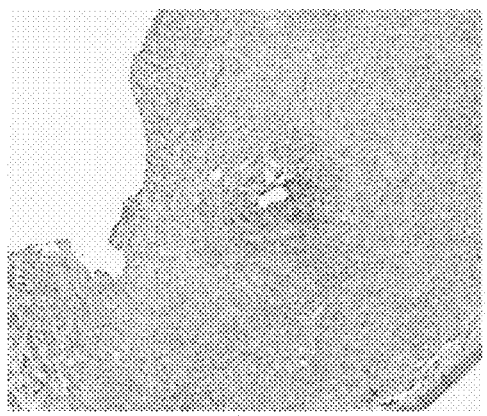
Figure 10D:
Figure 10E:
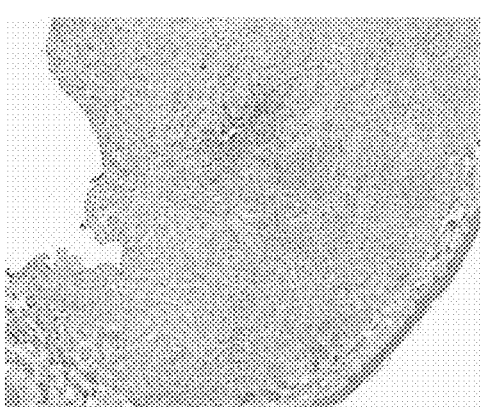
Figure 10F:
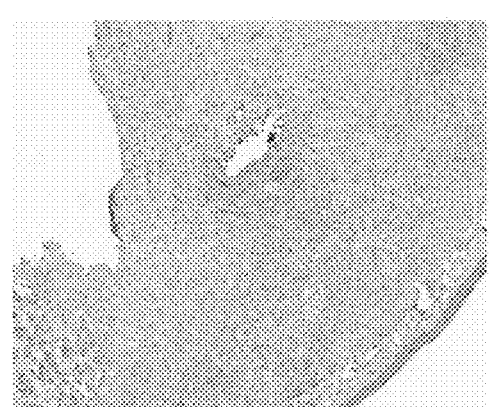
Figure 11A:
FIG. 11(A)-(F) are photomicrographs of serial microtome sections of a melanoma tissue sample showing the effect of reagent concentration and further increased clarification temperature on clarification results.
Figure 11B:
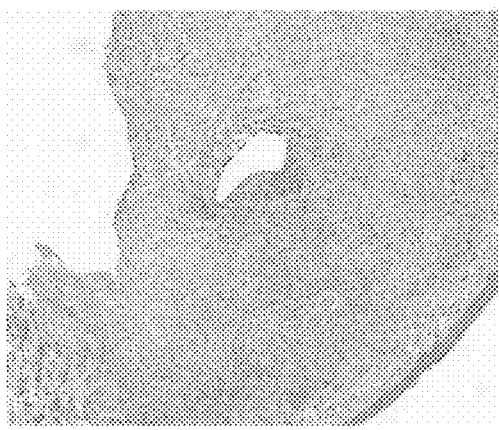
Figure 11C:
Figure 11D:
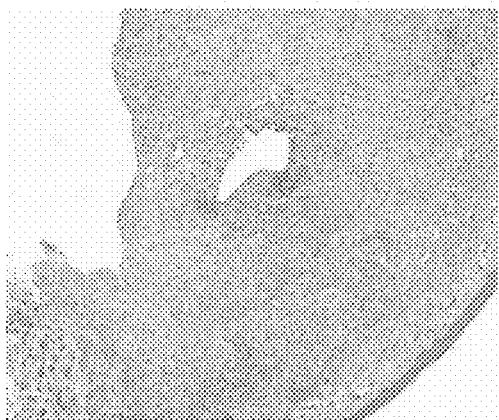
Figure 11E:
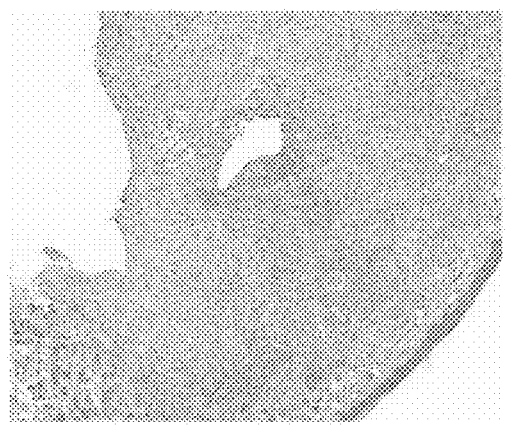
Figure 11F:

| Ex. # | Clarifying Step | Decolorization | Morphology | FIG. |
|---|---|---|---|---|
| 27 | 60° C. clarifying step with 3% H2O2 in 0.05M Sorensen's Phosphate Buffer pH 7.4 for 8 minutes | Incomplete | Maintained | FIG. 10(A) |
| 28 | 60° C. clarifying step with 6% H2O2 in 0.05M Sorensen's Phosphate Buffer pH 7.4 for 8 minutes | Incomplete | Maintained | FIG. 10(B) |
| 29 | 60° C. clarifying step with 9% H2O2 in 0.05M Sorensen's Phosphate Buffer pH 7.4 for 8 minutes | Nearly Complete | Maintained | FIG. 10(C) |
| 30 | 60° C. clarifying step with 3% H2O2 in 0.05M Sorensen's Phosphate Buffer pH 7.4 for 16 minutes | Incomplete | Maintained | FIG. 10(D) |
| 31 | 60° C. clarifying step with 6% H2O2 in 0.05M Sorensen's Phosphate Buffer pH 7.4 for 16 minutes | Nearly Complete | Maintained | FIG. 10(E) |
| 32 | 60° C. clarifying step with 9% H2O2 in 0.05M Sorensen's Phosphate Buffer pH 7.4 for 16 minutes | Complete | Maintained | FIG. 10(F) |
| 33 | 65° C. clarifying step with 3% H2O2 in 0.05M Sorensen's Phosphate Buffer pH 7.4 for 8 minutes | Incomplete | Maintained | FIG. 11(A) |
| 34 | 65° C. clarifying step with 6% H2O2 in 0.05M Sorensen's Phosphate Buffer pH 7.4 for 8 minutes | Incomplete | Maintained | FIG. 11(B) |
| 35 | 65° C. clarifying step with 9% H2O2 in 0.05M Sorensen's Phosphate Buffer pH 7.4 for 8 minutes | Nearly Complete | Maintained | FIG. 11(C) |
| 36 | 65° C. clarifying step with 3% H2O2 in 0.05M Sorensen's Phosphate Buffer pH 7.4 for 16 minutes | Nearly Complete | Maintained | FIG. 11(D) |
| 37 | 65° C. clarifying step with 6% H2O2 in 0.05M Sorensen's Phosphate Buffer pH 7.4 for 16 minutes | Complete | Maintained | FIG. 11(E) |
| 38 | 65° C. clarifying step with 9% H2O2 in 0.05M Sorensen's Phosphate Buffer pH 7.4 for 16 minutes | Complete | Maintained | FIG. 11(F) |

TABLE 5

Figure 12A:
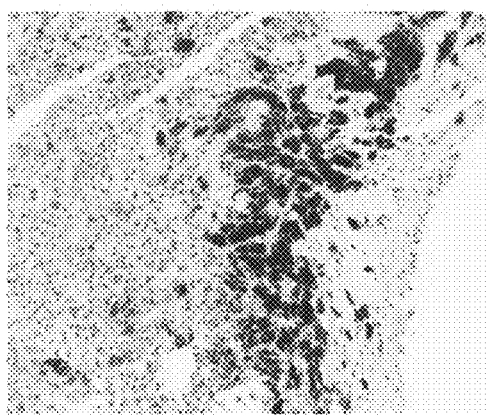
FIG. 12(A)-(F) are photomicrographs of serial microtome sections of a melanoma tissue sample showing the effect of clarification time on clarification results under fixed temperature and peroxide conditions.
Figure 12B:
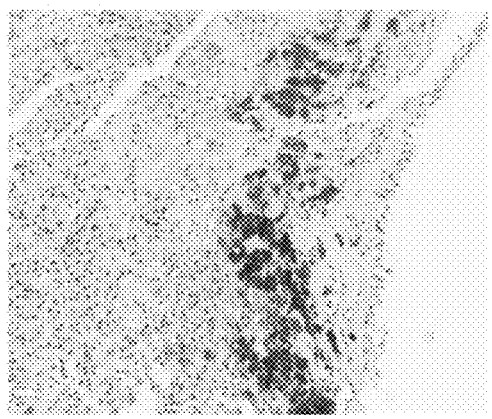
Figure 12C:
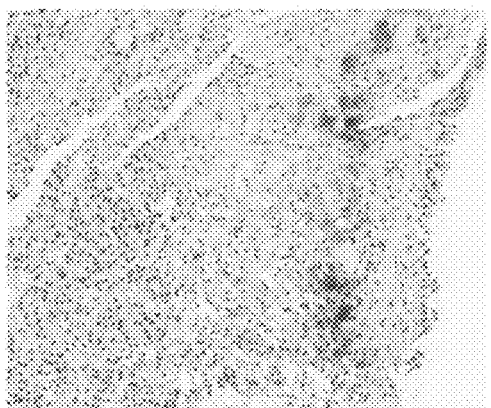
Figure 12D:
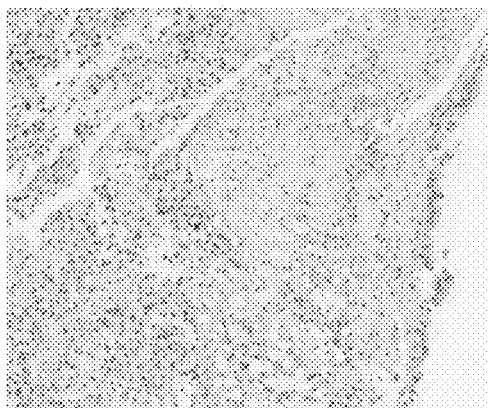
Figure 12E:
Figure 12F:

| Ex. # | Clarifying Step | Decolorization | Morphology | FIG. |
|---|---|---|---|---|
| 39 | No clarification step - control | None | Standard | FIG. 12(A) |
| 40 | 60° C. clarifying step with 9% H2O2 in 0.05M Sorensen's Phosphate Buffer pH 7.4 for 8 minutes | Incomplete | Maintained | FIG. 12(B) |
| 41 | 60° C. clarifying step with 9% H2O2 in 0.05M Sorensen's Phosphate Buffer pH 7.4 for 16 minutes | Incomplete | Maintained | FIG. 12(C) |
| 42 | 60° C. clarifying step with 9% H2O2 in 0.05M Sorensen's Phosphate Buffer pH 7.4 for 32 minutes | Nearly Complete | Maintained | FIG. 12(D) |
| 43 | 60° C. clarifying step with 9% H2O2 in 0.05M Sorensen's Phosphate Buffer pH 7.4 for 1 hour | Complete | Maintained | FIG. 12(E) |
| 44 | 60° C. clarifying step with 9% H2O2 in 0.05M | Complete | Maintained | FIG. 12(F) |

TABLE 5-continued

Figure 13A:
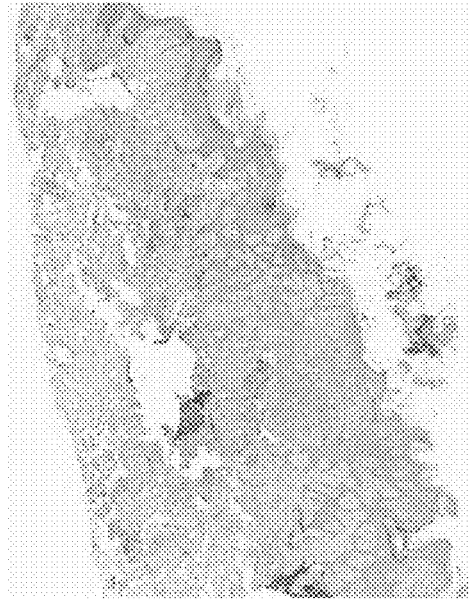
FIG. 13(A)-(D) are photomicrographs of serial microtome sections of a melanoma tissue sample showing the effect of the order of the clarification process within the overall staining procedure on clarification results.
Figure 13B:
Figure 13C:
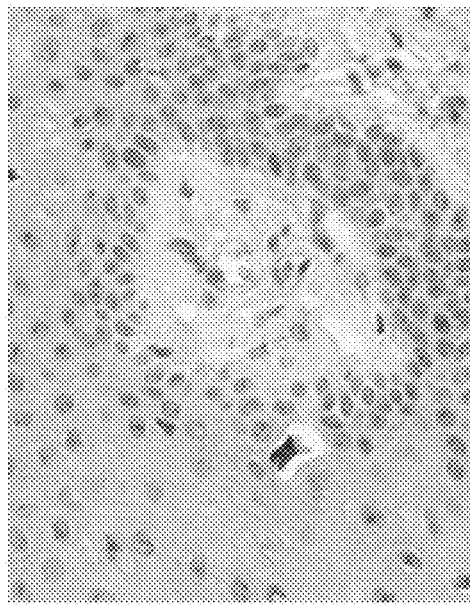
Figure 13D:
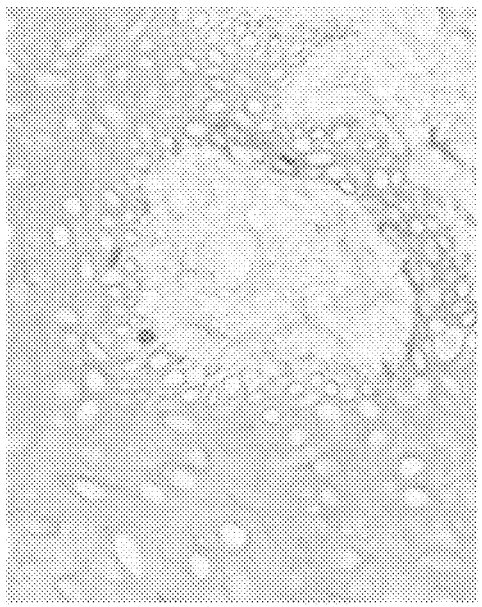

| Ex. # | Clarifying Step | Decolorization | Morphology | FIG. |
|---|---|---|---|---|
| | Sorensen's Phosphate Buffer pH 7.4 for 2 hours | | | |
| 39 | 60° C. clarifying step with 9% H2O2 in 0.05M Sorensen's Phosphate Buffer pH 7.4 for 8 minutes prior to staining | Complete | Maintained | FIG. 13(A) |
| 40 | 60° C. clarifying step with 9% H2O2 in 0.05M Sorensen's Phosphate Buffer pH 7.4 for 8 minutes subsequent to staining | Complete | Impaired | FIG. 13(B) |
| 41 | 60° C. clarifying step with 9% H2O2 in 0.05M Sorensen's Phosphate Buffer pH 7.4 for 8 minutes prior to staining | Complete | Maintained | FIG. 13(C) |
| 42 | 60° C. clarifying step with 9% H2O2 in 0.05M Sorensen's Phosphate Buffer pH 7.4 for 8 minutes subsequent to staining | Complete | Impaired | FIG. 13(D) |

Referring now to FIG. 5(A)-(E), Examples 1-5 are shown. FIG. 5(A)-(E) show serial sections of a heavily pigmented melanoma case incubated at 55° C. in 3% $H_2O_2$ for increasing amounts of time to assess the effect of duration of clarification on clarification efficacy and cell morphology. FIG. 5(A) shows the sample without clarification, showing the background level of pigmentation. FIG. 5(B) shows the sample having been clarified for 16 minutes, the photomicrograph showing significant, but incomplete clarification. FIG. 5(C) shows the sample having been clarified for 32 minutes, the photomicrograph showing significant and nearly complete clarification. FIG. 5(D) shows the sample having been clarified for 60 minutes, the photomicrograph showing complete clarification of the sample. FIG. 5(E) shows the sample having been clarified for 120 minutes, the photomicrograph showing complete clarification. Additionally, it is apparent from FIG. 5(E) that even 120 minutes of the clarification treatment does not noticeably degrade cell morphology.

Referring now to FIG. 6(A)-(E), examples 6-10 are shown. The photomicrographs show serial microtome sections of a different melanoma tissue sample showing the effect of clarification time for a heavily pigmented melanoma at 55° C. in 3% $H_2O_2$. FIG. 6(A) shows the sample with no clarification. The background level of pigmentation is apparent. FIG. 6(B) shows the sample clarified for 8 minutes; it is apparent that the conditions result in a small drop in pigment obfuscation. FIG. 6(C) shows a sample clarified for 16 minutes; it is apparent that the conditions result in significant, though incomplete, clarification. FIG. 6(D) shows the sample clarified for 32 minutes; it is apparent that the conditions result in removal of almost all obfuscation associated with the pigment. While not complete, it is contemplated that this level of clarification would enable certain stainings to be done without confusion. In particular, the amount of pigment left would not likely obscure reading of a genomic ISH signal. FIG. 6(E) shows a sample clarified for 60 minutes; it is apparent that the conditions result in complete clarification of the sample. Considering FIG. 6(A)-(E), it is evident that cell morphology is unaffected by the clarification conditions of examples 6-10.

Referring now to FIG. 7(A)-(E), examples 11-15 are shown. The photomicrographs show serial microtome sections of a different melanoma tissue sample showing the effect of clarification time for a heavily pigmented melanoma at 55° C. in 6% $H_2O_2$. FIG. 7(A) shows the sample with no clarification. The background level of pigmentation is apparent. FIG. 7(B) shows the sample clarified for 8 minutes; it is apparent that the conditions result in significant, though incomplete, clarification. FIG. 7(C) shows the sample clarified for 16 minutes; it is apparent that the conditions also result in significant, though incomplete, clarification. FIG. 7(D) shows the sample clarified for 32 minutes; it is apparent that the conditions result in complete clarification. FIG. 7(E) shows the sample clarified for 60 minutes; it is apparent that the conditions result in complete clarification of the sample. Considering FIG. 7(A)-(E), it is evident that cell morphology is unaffected by the clarification conditions of examples 11-15.

Referring now to FIG. 8(A)-(E), examples 16-20 are shown. The photomicrographs show serial microtome sections of a different melanoma tissue sample showing the effect of clarification time for a heavily pigmented melanoma at 55° C. in 9% $H_2O_2$. FIG. 8(A) shows the sample with no clarification. The background level of pigmentation is apparent. FIG. 8(B) shows the sample clarified for 8 minutes; it is apparent that the conditions result in significant, though incomplete, clarification. FIG. 8(C) shows the sample clarified for 16 minutes; it is apparent that the conditions also result in significant, though incomplete, clarification. FIG. 8(D) shows the sample clarified for 32 minutes; it is apparent that the conditions result in complete clarification. FIG. 8(E) shows a sample clarified for 60 minutes; it is apparent that the conditions result in complete clarification of the sample. Considering FIG. 8(A)-(E), it is evident that cell morphology is unaffected by the clarification conditions of examples 16-20. For those times monitored and for this type of sample, increasing $H_2O_2$ concentration to 9% does not result in a further reduction in the incubation time necessary for complete clarification.

Referring now to FIG. 9(A)-(F), examples 21-26 are shown. The photomicrographs show serial microtome sections of a melanoma tissue sample showing the effect of clarifying composition and time for a heavily pigmented melanoma at 55° C. in 3%, 6%, or 9% $H_2O_2$ for 8 or 16 minutes to assess the effect on clarification and cell morphology. FIG. 9(A) shows the sample clarified for 8 minutes in 3% $H_2O_2$. It is apparent that the clarification resulted in incomplete clarification. FIG. 9(B) shows the sample clarified for 8 minutes in 6% $H_2O_2$. Again, the sample appears significantly but incompletely clarified. FIG. 9(C) shows the sample clarified for 8 minutes in 9% $H_2O_2$. This process resulted in greater clarification than examples 21 or 22, but clarification remained incomplete. FIG. 9(D) shows the sample clarified for 16 minutes in 3% $H_2O_2$. This clarification resulted in significant though incomplete clarification. The level of clarification is greater than seen for experiment 21 (8 minute) shown in FIG. 9(A). FIG. 9(E) shows the sample clarified for 16 minutes in 6% $H_2O_2$. This experiment resulted in nearly complete clarification; it can be seen that the clarification is significantly greater than seen for experiment 22 (8 minute) as shown in FIG. 9(B). FIG. 9(F) shows the sample clarified for 16 minutes in 9% $H_2O_2$. This process resulted in nearly complete clarification, significantly greater than experiment 23 (8 minute) shown in FIG. 9(C). Overall, FIG. 9(A)-(F) demonstrates that independent of temperature both the $H_2O_2$ concentration and the incubation time affected clarification. The trends that are apparent are that clarification is more complete at increased $H_2O_2$ concentrations or at longer clarification times. Furthermore, cell morphology remained intact throughout all the experiments completed thus far (experiments 1-26). According to these trends, the most complete clarification was observed for the sample treated with the highest concentration of clarifier (9% $H_2O_2$) and the longest time (16 minutes).

Referring now to FIG. 10(A)-(F), examples 27-32 are shown. The photomicrographs show serial microtome sections of a melanoma tissue sample showing the effect of clarifying composition and time for a heavily pigmented melanoma at 60° C. in 3%, 6%, or 9% $H_2O_2$ for 8 or 16 minutes to assess the effect on clarification and cell morphology. FIG. 10(A) shows the sample clarified for 8 minutes in 3% $H_2O_2$. It is apparent that the clarification resulted in incomplete clarification. FIG. 10(B) shows the sample clarified for 8 minutes in 6% $H_2O_2$. Again, the sample appears significantly, but incompletely, clarified. FIG. 10(C) shows the sample clarified for 8 minutes in 9% $H_2O_2$. These conditions resulted in the sample nearing complete clarification. FIG. 10(D) shows the sample clarified for 16 minutes in 3% $H_2O_2$. This clarification resulted in significant though incomplete clarification. The level of clarification is greater than seen for experiment 27 (8 minute) shown in FIG. 10(A). FIG. 10(E) shows the sample clarified for 16 minutes in 6% $H_2O_2$. This experiment resulted in nearly complete clarification; it can be seen that the clarification is significantly greater than seen for experiment 28 (8 minute) as shown in FIG. 10(B). FIG. 10(F) shows the sample clarified for 16 minutes in 9% $H_2O_2$. This process resulted in nearly complete clarification, significantly greater than experiment 29 (8 minute) shown in FIG. 10(C). Overall, FIG. 10(A)-(F) demonstrate that, independent of temperature, both the $H_2O_2$ concentration and the incubation time are directly related to clarification. It is apparent that clarification is more complete at increased $H_2O_2$ concentrations or at longer clarification times. Furthermore, cell morphology remained intact throughout the experiments. According to these trends, the most complete clarification was observed for the sample treated with the highest concentration of clarifier (9% $H_2O_2$) and the longest time (16 minutes).

Referring now to FIG. 11(A)-(F), examples 33-38 are shown. The photomicrographs show serial microtome sections of a melanoma tissue sample showing the effect of clarifying composition and time for a heavily pigmented melanoma at 65° C. in 3%, 6%, or 9% $H_2O_2$ for 8 or 16 minutes, mirroring examples 27-32 at the elevated temperature of 65° C. The trends observed for examples 27-32, were similarly observed here except that the higher temperature results in slightly greater clarification under otherwise identical conditions. As a result, the sample shown in FIG. 11(A) exhibits significant though incomplete clarification, the sample shown in FIG. 11(B) exhibits significant though incomplete clarification, the sample shown in FIG. 11(C) exhibits nearly complete clarification, the sample shown in FIG. 11(D) exhibits nearly complete clarification, the sample shown in FIG. 11(E) exhibits complete clarification, and the sample shown in FIG. 11(F) results in complete clarification. Also of note is a lack of morphologic damage associated with the clarification conditions.

Referring now to FIG. 12(A)-(F), examples 39-44 are shown. The photomicrographs show serial microtome sections of a melanoma tissue sample showing the effect of clarifying a heavily pigmented melanoma at 60° C. in 9% $H_2O_2$ for 8, 16, 32, 60, and 120 minutes. The sample shown in FIG. 12(A) was not subjected to a clarification step and illustrates the endogenous level of pigment in the melanoma sample. FIG. 12(B) shows reduced obfuscation with an 8 minute clarification process; while reduced, the pigment is readily apparent. FIG. 12(C), the sample treated for 16 minutes, shows significant clarification, though the pigment remains apparent. FIG. 12(D), the sample treated for 32 minutes, shows nearly complete clarification. FIG. 12(E)-(F), the samples clarified for 60 and 120 minutes respectively, exhibit complete clarification. A lack of morphologic damage associated with the clarification is evident across the samples. From these results, clarification at 60° C. using a clarifying reagent containing 9% $H_2O_2$ clarifies a strongly pigmented melanoma between about 32 and 60 minutes.

Referring now to FIG. 13(A)-(D), show photomicrographs at low magnification (FIG. 13(A)-(B) (0.6×)) and high magnification (FIG. 13(C)-(D) (20×)) of two serial sections of a lightly pigmented melanoma that were incubated at 60° C. in 9% $H_2O_2$ for 8 minutes. The clarification was prior (FIGS. 13(A) and (C)) and subsequent (FIGS. 13(B) and (D)) to antibody staining. The photomicrographs of tissue samples processed with the clarification step prior to antibody staining indicate that tissue integrity is maintained. The photomicrographs of tissue samples processed with the clarification step subsequent to antibody staining indicate that tissue integrity is severely affected. In multiple areas, tissue loss is evident in FIG. 13(B). Higher magnification photomicrographs of the tissue processed with the clarification step prior to antibody staining show that cell morphology is unaffected, while the cell morphology of tissue processed with the clarification step subsequent to antibody staining was severely impaired, with nuclei no longer being discernable. The examples show that the order of the clarification step in the context of the staining procedure significantly contributes to the resulting tissue integrity.

BRAF V600E is an oncogenic BRAF mutation common in melanomas. The V600E substitution changes the activation segment of BRAF from inactive to active. Zelboraf (vemurafenib) has been shown to help people with the V600E mutation in metastatic melanoma and BRAF mutation testing is used to help select patients for treatment with vemurafenib. A V600E mutation can be detected by using a specific antibody, by DNA sequencing, or by using real-time PCR. Samples, having been characterized for BRAF V600E using DNA sequencing and PCR (COBAS® 4800 BRAF V600 Mutation Test) were analyzed using IHC with a BRAF V600E antibody. The samples were tested using a method that did and did not include a clarification step to probe the effect of the clarification procedure on the clinical interpretation. As such, the results of the clarified and obfuscated IHC were compared to the results obtained using DNA sequencing a PCR.

Figure 14A:
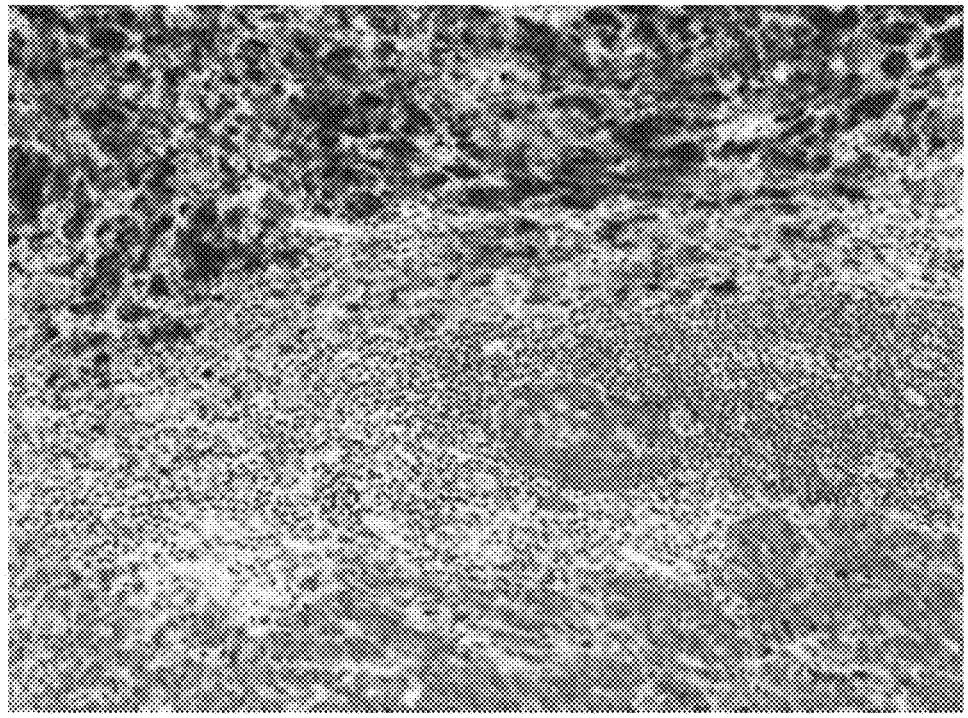
FIG. 14(A)-(B) are photomicrographs of a melanoma tissue sample tested for BRAF V600E status without clarification (A) and with (B) clarification.
Figure 14B:
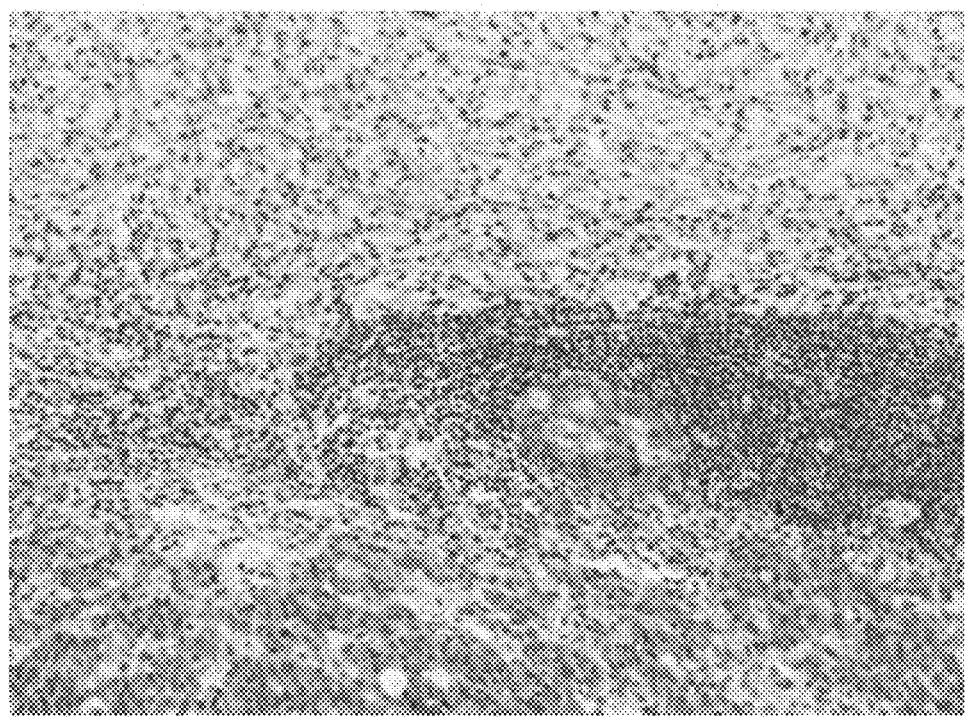

Referring now to FIG. 14(A)-(B), shown are photomicrographs of a melanoma tissue sample tested for BRAF V600E status. Reference is made to Table 6. Serial sections of a highly pigmented melanoma case were stained with the anti-BRAF V600E antibody either without clarification FIG. 14(A) or with clarification FIG. 14(B). Without clarification, the melanin pigment obscured the specific V600E staining.

After clarification, only specific V600E staining remains, allowing an unambiguous determination of V600E status. As described in Table 6, the two standard V600E tests, DNA sequencing (V600E positive) and PCR (V600E negative), disagreed on V600E status. Automated IHC that includes a clarification process was used to obtain a clear V600E staining.

TABLE 6

Figure 15A:
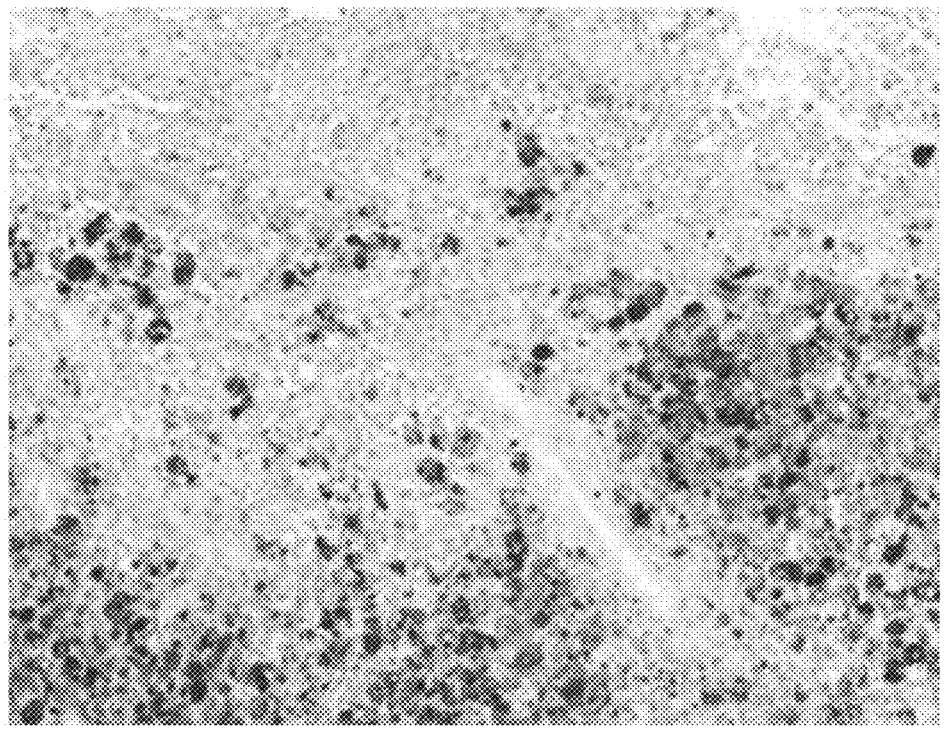
FIG. 15(A)-(B) are photomicrographs of a melanoma tissue sample tested for BRAF V600E status without clarification (A) and with (B) clarification.
Figure 15B:
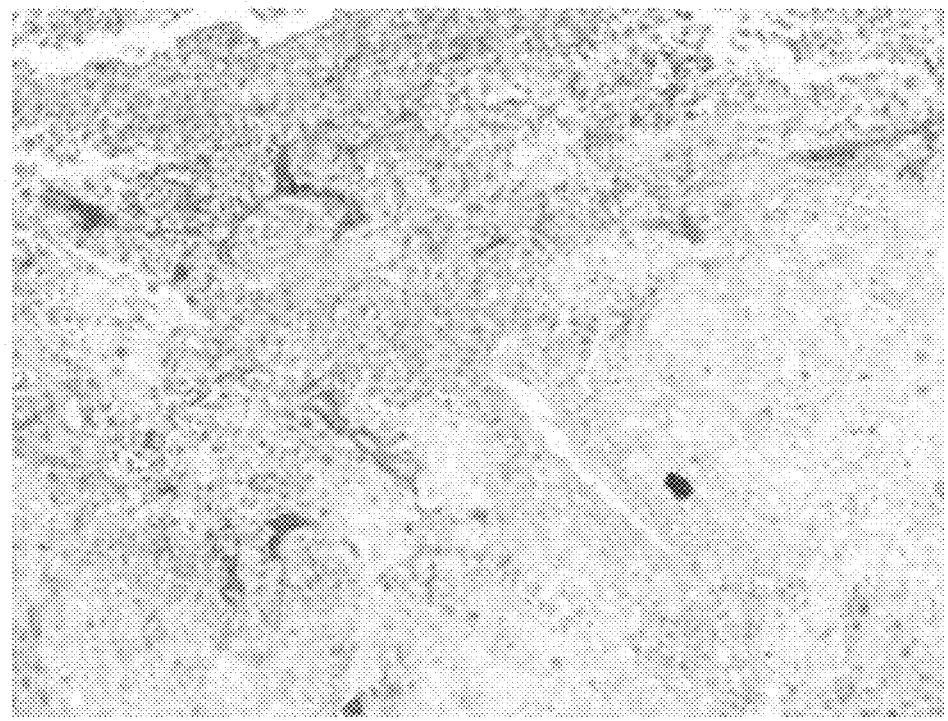
Figure 16A:
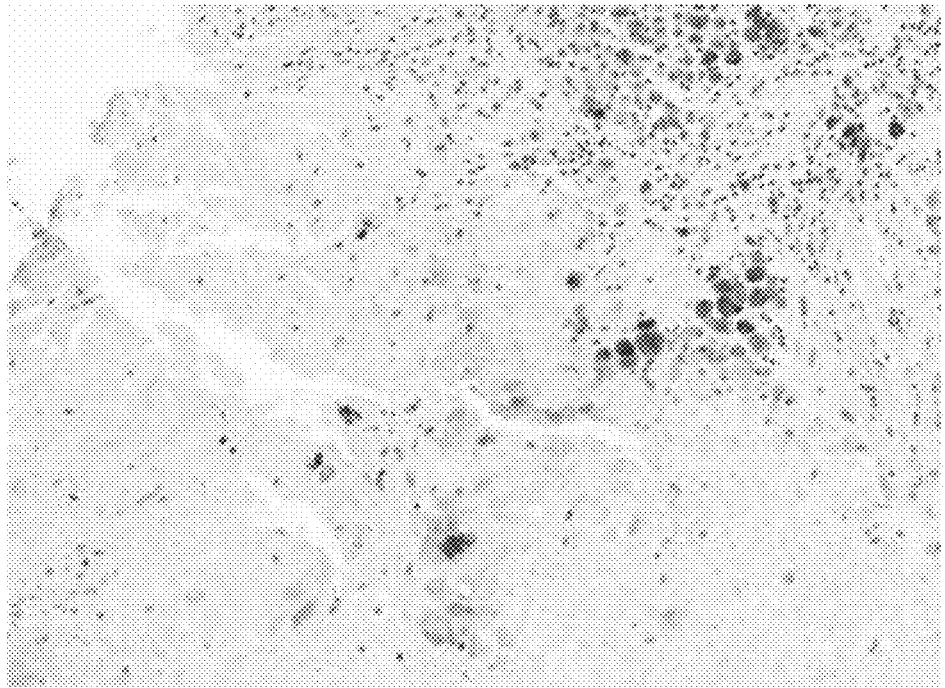
FIG. 16(A)-(B) are photomicrographs of a melanoma tissue sample tested for BRAF V600E status without clarification (A) and with (B) clarification.
Figure 16B:
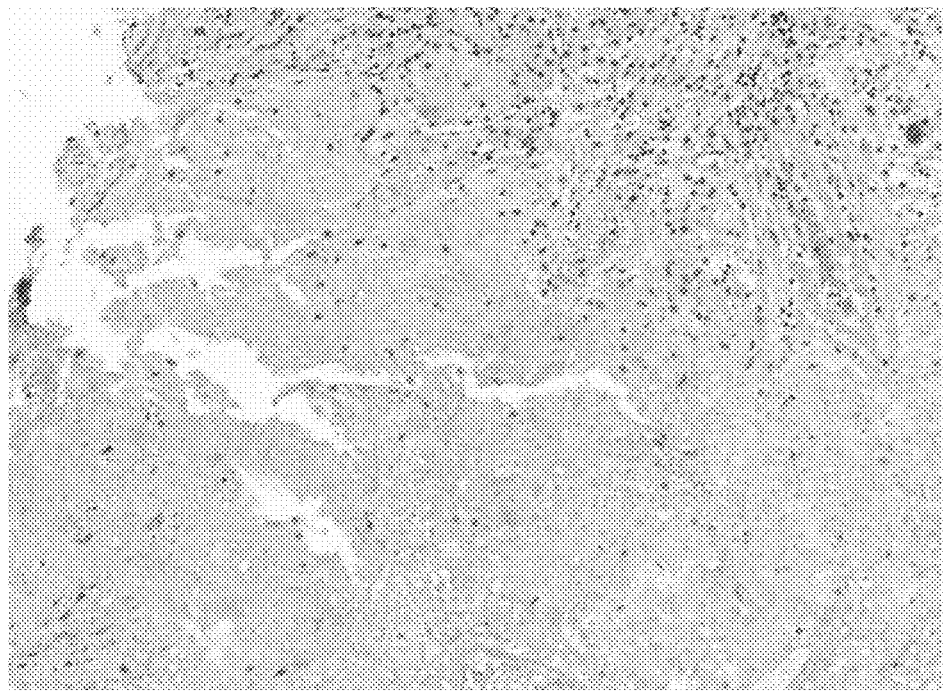
Figure 17A:
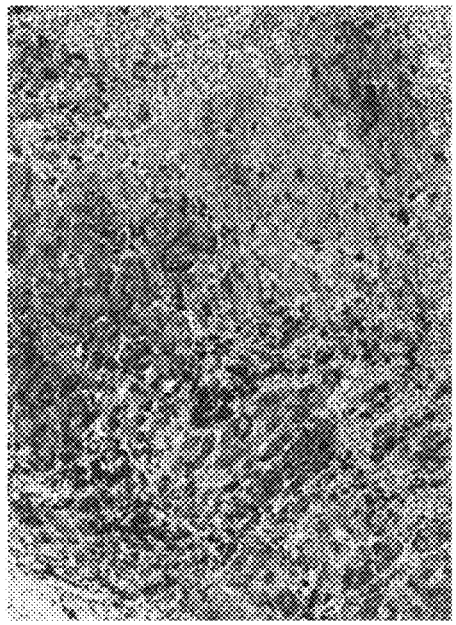
FIG. 17(A)-(D) are photomicrographs of a melanoma tissue sample tested for BRAF V600E status, showing (A) a V600E positive region without clarification, (B) a V600E positive region with clarification, (C) a V600E negative region without clarification, and (D) a V600E negative region with clarification.
Figure 17B:
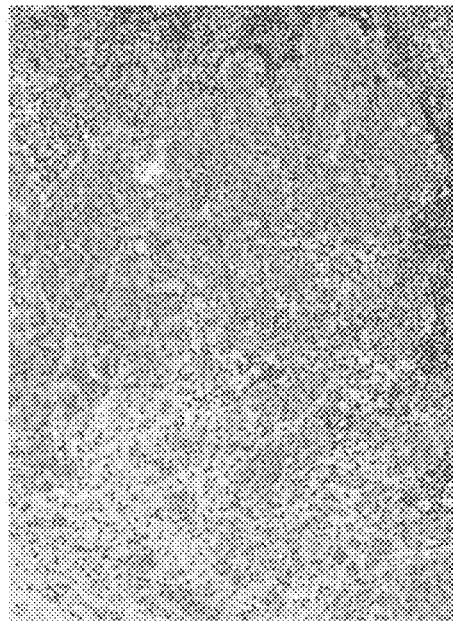
Figure 17C:
Figure 17D:

| Sample | DNA Seq. | PCR | IHC | Clarified IHC |
|---|---|---|---|---|
| 1 | Positive | Negative | Positive - FIG. 14(A) | Positive - FIG. 14(B) |
| 2 | Positive | Positive | Positive - FIG. 15(A) | Positive - FIG. 15(B) |
| 3 | Positive | Positive | Negative - FIG. 16(A) | Positive - FIG. 16(B) |
| 4 | Negative | Negative | Positive - FIG. 17(A) | Positive - FIG. 17(B) |
| 4 | Negative | Negative | Obscured - FIG. 17(C) | Negative - FIG. 17(D) |

Referring now to FIG. 15(A)-(B), shown are photomicrographs of a melanoma tissue sample tested for BRAF V600E status. These photomicrographs show application of a clarification procedure during IHC to determine the BRAF V600E status in a highly pigmented melanoma specimen. Serial sections of the melanoma case were stained with the anti-BRAF V600E antibody either without clarification FIG. 15(A) or with clarification FIG. 15(B). Without clarification, melanin pigment obscures whether specific V600E staining has occurred. After clarification, only specific V600E staining remains. This allows for an unambiguous determination of V600E status. In this particular case, DNA sequencing (V600E positive) and PCR (V600E positive) agreed with clarified IHC with respect to V600E status. Clarification allowed for clear confirmation of these results and demonstrated concordance with the accepted methods for testing V600E status.

Referring now to FIG. 16(A)-(B), shown are photomicrographs of a melanoma tissue sample tested for BRAF V600E status. Serial sections of the melanoma case were stained with the anti-BRAF V600E antibody either without clarification FIG. 16(A) or with clarification FIG. 16(B). Without clarification, melanin pigment obscures whether specific V600E staining has occurred and in this case the staining was misinterpreted as V600E negative. After clarification, only specific V600E staining remains. This allows for an unambiguous determination of V600E status. As such, a qualified pathologist read FIG. 16(B) as V600E positive. DNA sequencing (V600E positive) and PCR (V600E positive) agreed with clarified IHC with respect to V600E status. Clarification prevented the sample from being mis-classified.

Referring now to FIG. 17(A)-(D), shown are photomicrographs of a melanoma tissue sample tested for BRAF V600E status. In these examples, the clarification procedure assists in determining BRAF V600E status in a highly pigmented melanoma specimen that appears to be heterogeneous for V600E expression. Serial sections of the melanoma case were stained with the anti-BRAF V600E antibody either without clarification (FIGS. 17(A) and (C)) or with clarification (FIGS. 17(B) and (D)). Without clarification, melanin pigment obscures or may be confused with specific V600E staining. In some small highly pigmented areas, clarification clearly shows regions of V600E staining (i.e. while FIG. 17(A) is unclear, FIG. 17(B) is clearly V600E positive). In most other areas of the tumor that are highly pigmented (e.g. FIG. 17(C)) clarification reveals a negative V600E status (e.g. FIG. 17(D)). For these samples, DNA sequencing and PCR both returned a V600E negative result. While these results were technically correct for portions of the sample, the heterogeneity of the sample would result in a mis-classification of the tumors. This occurrence is even more likely if the V600E positive regions represent only very small portions of a larger tumor. Clarification of the melanoma sample allowed for clear visualization of the heterogeneous nature of this tumor and identification of small pockets of V600E staining within the larger V600E negative tumor body.

The invention claimed is:

1. An automated method of treating a sample mounted on a substrate to alleviate staining obfuscations associated with pigments within the sample, the method comprising the following steps in the following order:
   (a) applying a clarifying reagent in an amount sufficient to contact the sample and decolorize the pigments in said sample, wherein application of the clarifying reagent includes mixing to agitate the clarifying reagent while in contact with the sample;
   (b) applying a rinsing reagent so that the clarifying reagent is substantially removed from contacting the sample,
   (c) applying a cell conditioning reagent for antigen retrieval subsequent to applying the clarifying reagent, the cell conditioning reagent contacts the sample; and
   (d) applying a chromogenic reagent subsequent to applying the cell conditioning reagent, the chromogenic reagent is applied so that the sample is specifically stained;
   wherein the pigments within the sample are decolorized so that the specifically stained sample is interpretable by a qualified reader.

2. The method of claim 1 further comprising applying heat to the substrate so that the sample and the clarifying reagent are maintained at a predetermined temperature while in contact.

3. The method of claim 2, wherein the predetermined temperature is between about 35° C. and about 100° C., between about 40° C. and about 90° C., between about 45° C. and about 80° C., or between about 50° C. and about 70° C.

4. The method of claim 2, wherein the substrate is a glass slide and a heated slide platform is used for applying heat to the glass slide.

5. The method of claim 4, wherein the heated slide platform has a uniformity in temperature across the slide of less than about plus or minus 2° C. at 37° C. and less than about plus or minus about 4° C. at 100° C. or the uniformity in temperature across the slide is less than about plus or minus 2° C. at 37° C. and less than about plus or minus about 3° C. at 100° C.

6. The method of claim 4, wherein the sample can be increased in temperature from 37° C. to 100° C. within eight (8) minutes and cooled from 100° C. to 50° C. within eight (8) minutes or the sample can be increased in temperature from 37° C. to 100° C. within four (4) minutes and cooled from 100° C. to 37° C. within eight (8) minutes.

7. The method of claim 1, wherein the automated method is devoid of steps requiring a user to handle the substrate between placing the substrate upon which the sample is mounted on the automated instrument and contacting the sample with the chromogenic reagent such that the sample is specifically stained.

8. The method of claim 1, wherein the step of applying the clarifying reagent, the step of applying the rinsing reagent, and the step applying the chromogenic reagent are walk-away fully-automated functions of the automated instrument.

9. The method of claim 1, wherein the step of applying the clarifying reagent includes the clarifying reagent contacting the sample for a time between about 2 minutes and about 2 hours, between about 4 minutes and about 1.5 hours, between about 6 minutes and about 1 hour, or between about 8 minutes and about 0.5 hours.

10. The method of claim 1, wherein the step of applying the clarifying reagent does not include submersing the substrate in a bath.

11. The method of claim 1, wherein the step of applying the clarifying reagent includes an amount of the clarifying reagent of between about 0.05 mL and about 3 mL, between about 0.1 mL and about 1.5 mL, between about 0.2 mL and about 1 mL, or between about 0.3 mL and about 0.5 mL.

12. The method of claim 1, further comprising applying an immunohistochemical binding reagent or an in situ hybridization binding reagent so that the immunohistochemical binding reagent or the in situ hybridization binding reagent contact the sample.

13. The method of claim 12, wherein the applying the immunohistochemical binding reagent or the in situ hybridization binding reagent occurs subsequently to the step of applying the cell condition reagent and prior to the step of applying the chromogenic reagent.

14. The method of claim 1 further comprising applying a buffered preparatory solution so that the buffered preparatory solution contacts the sample prior to applying the clarifying reagent.

15. The method of claim 1, wherein the clarifying reagent includes about 1% to about 12% hydrogen peroxide (v/v), about 2% to about 10% hydrogen peroxide (v/v), or about 3% to about 9% hydrogen peroxide (v/v).

16. The method of claim 1, wherein the clarifying reagent includes a phosphate buffer at a concentration of about 0.001 M to about 0.5 M, about 0.01 M to about 0.1 M, or about 0.05 M.

17. The method of claim 1, wherein the clarifying reagent is buffered at a pH of between about 3 to about 11, between about 4 to about 10, between about 5 to about 9, between about 6 to about 8, or about 7.

18. The method claim 1, wherein the clarifying reagent includes a Sorensen's buffer at a concentration of about 0.001 M to about 0.5 M, about 0.01 M to about 0.1 M, or about 0.05 and a pH of between about 4 to about 10, between about 5 to about 9, between about 6 to about 8, or about 7.

19. The method of claim 1, wherein interpretable by the qualified reader includes the sample exhibiting morphological characteristics consistent with those of the sample prior to the applying the clarifying reagent.

20. The method of claim 1, wherein interpretable by the qualified reader includes the sample exhibiting antigenic and genetic characteristics consistent with or improved with respect to those of the sample prior to applying the clarifying reagent.

21. The method of claim 1 further comprising applying a protease reagent so that the protease reagent contacts the sample.

22. The method of claim 1, wherein applying the clarifying reagent includes applying drops of the clarifying reagent onto the sample or applying drops of the clarifying reagent in the vicinity of the sample and forcing the drops to contact with the sample in a turbulent flow regime.

23. The method of claim 22, wherein the drops of the clarifying reagent have a volume of between about 0.05 mL and about 3 mL, between about 0.1 mL and about 1.5 mL, between about 0.2 mL and about 1 mL, or between about 0.3 mL and about 0.5 mL.

24. The method of claim 1, further comprising applying a second clarifying reagent so that the second clarifying reagent contacts the sample subsequent to applying the clarifying reagent and prior to applying the chromogenic reagent.

* * * * *